(12) United States Patent
Charles et al.

(10) Patent No.: US 6,330,837 B1
(45) Date of Patent: Dec. 18, 2001

(54) PARALLEL MECHANISM

(75) Inventors: Steve T. Charles, Germantown, TN (US); Robert S. Stoughton, Albuquerque, NM (US)

(73) Assignee: MicroDexterity Systems, Inc., Memphis, TN (US)

( * ) Notice: Subject to any disclaimer, the term of this patent is extended or adjusted under 35 U.S.C. 154(b) by 0 days.

(21) Appl. No.: 09/486,287

(22) PCT Filed: Aug. 27, 1998

(86) PCT No.: PCT/US98/17722

§ 371 Date: May 16, 2000

§ 102(e) Date: May 16, 2000

(87) PCT Pub. No.: WO99/10137

PCT Pub. Date: Mar. 4, 1999

Related U.S. Application Data

(60) Provisional application No. 60/056,237, filed on Aug. 28, 1997.

(51) Int. Cl.[7] ............................. B25J 11/00; B25J 17/02
(52) U.S. Cl. ......................... 74/490.06; 901/22; 901/23; 901/29
(58) Field of Search .......................... 74/490.06; 901/22, 901/23, 29

(56) References Cited

U.S. PATENT DOCUMENTS

| | | | |
|---|---|---|---|
| 3,923,166 | * | 12/1975 | Fletcher et al. . |
| 5,053,687 | * | 10/1991 | Merlet . |
| 5,081,381 | * | 1/1992 | Narasaki . |
| 5,354,158 | * | 10/1994 | Sheldon et al. . |
| 5,397,323 | * | 3/1995 | Taylor et al. . |
| 5,425,616 | * | 6/1995 | Arai et al. . |
| 5,800,423 | * | 9/1998 | Jensen . |
| 5,943,914 | * | 8/1999 | Morimoto et al. . |
| 5,976,156 | * | 11/1999 | Taylor et al. . |
| 6,000,297 | * | 12/1999 | Morimoto et al. . |

FOREIGN PATENT DOCUMENTS

0009447 * 4/1980 (EP) .

* cited by examiner

Primary Examiner—Allan D. Herrmann
(74) Attorney, Agent, or Firm—Leydig, Voit & Mayer, Ltd.

(57) ABSTRACT

A parallel mechanism is capable of positioning and orienting an end platform with up to six or more degrees of freedom. In preferred embodiments, the mechanism includes six links having a first and second ends. The first end is connected to an end platform for supporting a tool, while the second end is connected to an actuator capable of translating the second end. A rotational drive mechanism may be provided for rotating an object mounted on the end platform at varying orientations of the end platform independently of movement of the end platform as a whole. The links may be curved in order to avoid interference between adjoining links, thereby permitting an increased range of motion and improved dexterity of the mechanism.

29 Claims, 15 Drawing Sheets

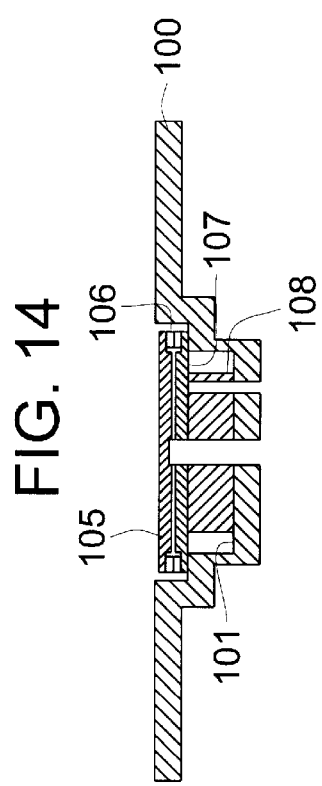
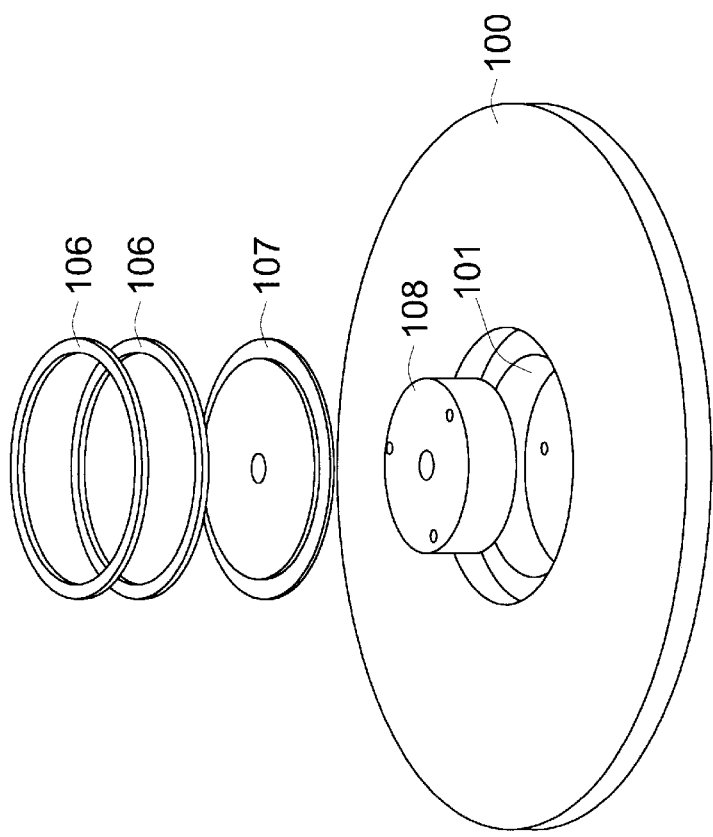

PARALLEL MECHANISM

This application is a 371 of PCT/US98/17722 filed Aug. 27, 1998 which claims benefit of Prov. No. 60/056,237 filed Aug. 28, 1997.

BACKGROUND OF THE INVENTION

1. Field of the Invention

The present invention relates to multiple degree-of-freedom (DOF) parallel mechanisms which can provide quick and precise manipulative capabilities.

2. Description of the Related Art

The vast majority of multiple degree-of-freedom mechanisms that are used in robotic or teleoperator applications are so-called serial mechanisms. A serial mechanism is one in which a plurality of links are connected together in series to form an open chain and are moved with respect to each other by actuators connected between them to manipulate an object supported at the remote end of the chain of links. This type of mechanical mechanism has the advantages of the ability to access large workspaces, and of simplicity of design and geometric analysis. It has been shown that the forward kinematic problem is always directly solvable for serial mechanisms. The forward kinematic problem is defined as the task of solving for the position and orientation of the remote end of the mechanism on which a tool is mounted, given the lengths of all of the links and the angles between adjoining links.

Despite the above mentioned advantages, serial mechanisms are inherently plagued with a number of disadvantages. For one, the links at the base of a serial mechanism must support all of the more remote links of the mechanism. As a result, large actuators are required to drive the actuated joints at the base of the mechanism. For precise control, it is advantageous to have an actuator as close as possible to the tool or other object being driven by the actuator. With a serial mechanism, having an actuator close to the object being driven compromises the overall performance of the mechanical system, since actuators are typically heavy electric motors. In the case of a robotic wrist, for example, the designer must choose between locating the actuators that drive the robotic wrist directly at the wrist joints, and locating the wrist actuators towards the base of the robot and using a complex series of cables, gears, or other transmission devices to connect the wrist actuators to the wrist joints. The former choice allows precise control of the wrist but also requires that elbow and shoulder actuators located closer to the base support these wrist actuators, resulting in a large load being applied to the elbow and shoulder actuators. The latter choice reduces the moving mass which the elbow and shoulder actuators of the robot must support, but it also introduces numerous potential sources of error in the control of the position and/or force of the wrist, including backlash, friction, and wear. Another problem of serial mechanisms occurs when the position of the mechanism remote from a support structure is determined by sensors, such as encoders, which are located at the joints of the mechanism and measure the angles between adjoining links. Errors in measurement by the encoders are cumulative, i.e., the error in the calculated position of the remote end of the mechanism is a sum of errors of the individual encoders, so it is difficult to determine the position of the remote end with accuracy. Even when there is no encoder error, calculation of the position of the remote end may be inaccurate due to bending of the links forming the serial mechanism. These problems occur not just with robotic wrists but with serial mechanisms in general.

Another variety of multiple degree-of-freedom mechanism is referred to as a parallel mechanism. In parallel mechanisms, a plurality of actuators drive a tool or other object in "parallel", typically via a plurality of stiff links and joints. The term parallel in this sense means that the links share the load being supported by the mechanism, and it does not require that the links be geometrically parallel or imply that they are. Parallel mechanisms are inherently stiffer, quicker, more accurate, and capable of carrying higher loads than serial mechanisms. This is because parallel mechanisms have multiple mechanical ties between a base support structure and the object being supported so that the weight of the object is divided among a plurality of members, whereas in serial mechanisms, each link must support the entire weight of the object. A well-known example of a parallel mechanism is the Stewart Platform in which a load is supported by a plurality of links which can be adjusted in length by actuators to vary the position and orientation of the load. A parallel mechanism typically has all of its actuators mounted either on or relatively close to a base support structure, so the actuators either do not move or move very little during the operation of the mechanism. This minimizes the moving mass of the mechanism, making it much quicker than an equivalent serial mechanisms. Furthermore, since the entire load carried by the mechanism is not applied to each actuator as in a serial mechanism but is distributed among the actuators, the load capacity of the mechanism can be greatly increased relative to that of a serial mechanism without requiring large capacity (and thus bulky and heavy) actuators. In addition, errors in encoders or other sensors for sensing the position or orientation of the links forming a parallel mechanism are averaged rather than summed as in a serial mechanism, so the position and orientation of a load can be determined with high accuracy. A parallel mechanism is akin to a truss or space frame-type structure in which a load is supported by multiple paths to ground rather than by a single path. A mechanism is considered fully parallel if it has no actuators connected in series.

In spite of such advantages, parallel mechanisms have not achieved widespread acceptance as robotic or teleoperated devices due to a number of drawbacks. One is that conventional parallel mechanisms have limited reachable workspaces compared to serial mechanisms, so they are limited to tasks which do not require large workspaces. This is in part because parallel mechanisms have multiple mechanical ties to a fixed support structure whereas serial mechanisms have only one, and in part because the parallel links of a parallel mechanism can interfere with one another in certain positions. In addition, the forward kinematics problem for a parallel mechanism can be extremely complex mathematically, and in many cases it is not solvable, often making real time control of a parallel mechanism difficult or impossible.

Aside from the above problems, both parallel and serial mechanisms of conventional design tend to suffer from backlash in the components, relatively high friction, a narrow operational bandwidth, and high inertia which make high positional resolution and highly sensitive force control difficult to achieve.

SUMMARY OF THE INVENTION

The present invention provides a parallel mechanism for robotic or teleoperator (master/slave) applications which can operate with six or more degrees of freedom and which can overcome many of the disadvantages of known parallel mechanisms.

According to one form of the present invention, a parallel mechanism for manipulating an object includes a platform for supporting an object to be manipulated, a plurality of links each having a first end rotatably connected to the platform and a second end spaced from the platform with the platform being kinematically restrained by the links, and a plurality of linear motors each associated with one of the links for translating the first end of the corresponding link to move the platform. The use of linear motors to translate the links enables smooth, precise control of the movement of the mechanism and/or the force exerted by the mechanism, making it highly suitable for use in the assembly or manipulation of delicate objects. Linear motors also help to give the mechanism a low inertia, which is highly advantageous from the standpoint of speed and accuracy of control.

According to another form of the present invention, a parallel mechanism for manipulating an object includes a platform for supporting an object to be manipulated, a plurality of links each having a first end rotatably connected to the platform and a second end spaced from the platform with the platform being kinematically restrained by the links, an actuator associated with each link for translating the first ends of the links to move the platform, and a rotatable support member rotatably mounted on the platform for supporting an object to be manipulated. In preferred embodiments, the rotatable support member comprises a rotatable tool plate mounted on the platform. The support member is preferably rotated by a drive member which is spaced from the platform and coupled to the support member in a manner enabling the drive member to rotate the support member with respect to the platform at varying angles and positions of the platform relative to the drive member. The rotatable support member enables an object supported by it to be rotated by a greater amount and at a faster speed than is possible by movement of the links alone. Furthermore, the support member can prevent an object supported by it from rotating while the rotational position of the platform is adjusted.

According to yet another form of the present invention, a parallel mechanism includes a plurality of links connected to a platform for supporting an object to be manipulated with the platform being kinematically restrained by the links, with at least one of the links being a nonlinear link having a portion not coinciding with a straight line between its first and second ends. Nonlinear links increase the range of movement of the platform before links interfere with each other, resulting in a larger workspace for the mechanism, as well as the ability to employ link geometries giving the mechanism high dexterity.

According to still another form of the present invention, a parallel mechanism includes six links having first and second rotatable joints at its opposite ends, with the first joints connecting the links to a platform for supporting an object to be manipulated and with the platform being kinematically restrained by the links. The centers of rotation of the first joints are spaced at substantially equal angular intervals about a first axis, and the centers of rotation of the second joints are spaced at substantially equal angular intervals about a second axis when the mechanism is in a reference position. Having the joints equally spaced about the axes results in high dexterity, meaning that the mechanism can apply roughly the same forces and moments in any direction and enables the mechanism to be as compact as possible.

A parallel mechanism according to the present invention is capable of having a high mechanical bandwidth, a low inertia, a high dexterity, and low frictional resistance, all of which combine to enable it to operate with a high degree of position and force control unattainable by conventional serial or parallel mechanisms.

A parallel mechanism according to the present invention can be used in any application in which an object needs to be manipulated in space with one or more degrees of freedom. A few examples of possible applications in various fields are as follows.

Industrial Applications

A parallel mechanism according to the present invention can be used as a general purpose manipulator or a robotic arm for manipulating any desired device in an industrial application, including parts to be assembled, workpieces being processed, manufacturing tools (cutting tools, welding tools, sensors, painting equipment, etc.), and sensors (cameras, distance sensors, movement sensors, temperature sensors, etc.) for forming images or gathering other information about the work environment in which the mechanism is located. When the mechanism is equipped with a rotatable tool plate, the tool plate can be used to rotate a workpiece or a tool for various purposes including drilling, screw driving, fastening, milling, deburring, and tightening. The mechanism is capable of being miniaturized as well as being made as large as desired, so it can be used in applications ranging from heavy industrial applications down to microassembly or micromachining.

Medical Applications

The end platform of a parallel mechanism according to the present invention can be used to support a medical device, such as a diagnostic device or a surgical tool. Because the links and the end platform can be made extremely small, the mechanism can be used either for surgery through a large surgical opening or for endosurgery through a small surgical opening or body orifice. Because the end platform is capable of being manipulated with high accuracy and dexterity and can provide force feedback to the user, the parallel mechanism is particularly suitable for use in surgery by remote control. The ability of the mechanism to adjust the position of the end platform with a resolution on the order of nanometers makes the mechanism highly suitable for medical applications requiring precise, fine motions, and particularly for microsurgery performed with the aid of a microscope, including eye surgery, ear, nose and throat surgery, neurosurgery, and micro-hand or micro-orthopedic surgery.

Support Device

Because of its stiffness and ability to dynamically adjust the position of a load, the parallel mechanism can be used as a general purpose support. For example, it can be used to support a camera, a surveying instrument, or a telescope.

Control Device

A parallel mechanism according to the present invention can be used as a master control device with up to six or more degrees of freedom in a master-slave system. Instead of the end platform being used to support a load, the end platform or a handle attached to the end platform can be grasped by a user who manipulates the end platform like a joy stick in a desired manner. The movement of the ends of the links remote from the end platform or changes in the lengths of the links resulting from the movement of the end platform can be sensed to determine the movement of the end platform of the master, and commands for controlling the slave mechanism can be generated based on the sensed movement of the master. A parallel mechanism according to the present invention is particularly suitable as a master control device when the slave device which is to be controlled is another parallel mechanism according to the present invention.

Construction and Maintenance

A parallel mechanism according to the present invention can be used in a manner similar to a conventional crane or "cherry picker" to support equipment, materials, or workers.

BRIEF DESCRIPTION OF THE DRAWINGS

FIG. 13 is an exploded isometric view of the end platform of the embodiment of FIG. 8.

FIG. 14 is a vertical cross-sectional view of the end platform of FIG. 13.

DESCRIPTION OF PREFERRED EMBODIMENTS

Figure 1:
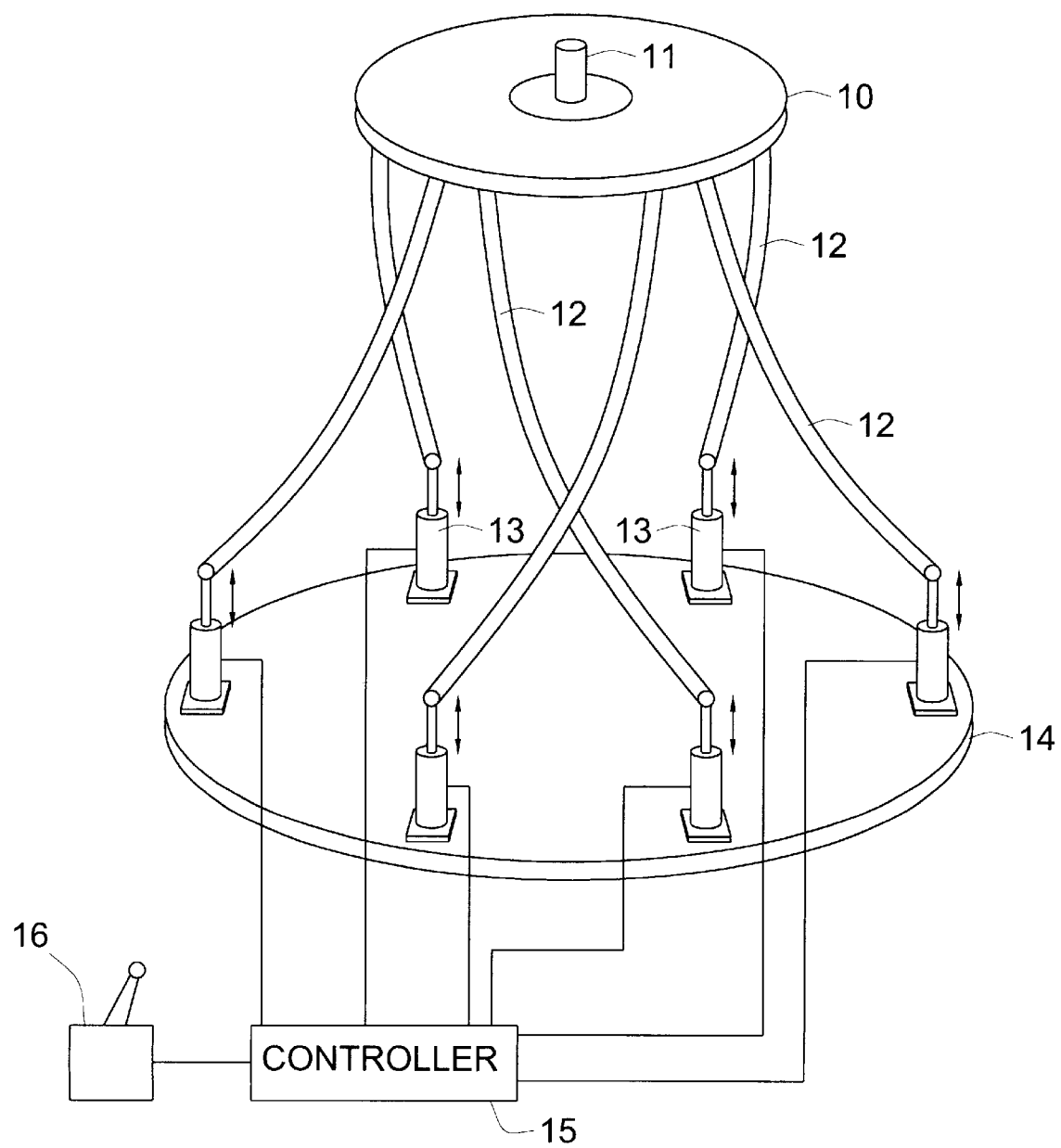
FIG. 1 schematically illustrates an embodiment of a parallel mechanism according to the present invention having fixed-length passive links.

FIG. 1 schematically illustrates an embodiment of a parallel mechanism according to the present invention. This embodiment includes an end platform 10 which can be used to support and manipulate a load 11, such as a tool, a sensor, a workpiece, or any other member which it is desired to support and manipulate in space. The end platform 10 is in turn supported by a plurality of links 12, each of which has a first end pivotably connected to the end platform 10 and a second end pivotably connected to an actuator 13 which is capable of translating the second end and exerting a force on the end platform 10 through the link 12. The actuators 13 are supported atop a suitable support member 14, which may be a stationary member, such as a rigid base or table, or it may be a movable member, such as a robotic arm. The actuators 13 are controlled by a controller 15 which controls the operation of the actuators 13 either autonomously to enable the mechanism to function as an autonomous robot, or based on an input from a suitable input device, such as a joy stick 16. Operation of the actuators 13 to translate the second ends of the links 12 changes the position of the first ends of the links 12 to change the position and/or orientation of the end platform 10 supported by the links 12. The mechanism is shown in FIG. 1 as being substantially vertically oriented with the end platform 10 located above the actuators 13, but the mechanism can have any desired orientation with respect to the vertical permitted by the rigidity of the links 12.

The links 12 are typically rigid members capable of transmitting a compressive load, although if the end platform 10 is always located beneath the actuators 13, the links 12 may be tension members, such as flexible cables, which only support a tensile load. In the mechanism shown in FIG. 1, the links 12 are of the type referred to as passive links, meaning that the lengths of the links 12 normally remain constant during operation of the mechanism (ignoring changes in length due to stresses and temperature), with movement of the end platform 10 being achieved by translation of both ends of the links 12 rather than by a change in the lengths of the links. However, passive links need not be incapable of changes in length and may include adjusting screws or other mechanisms which enable their lengths to be adjusted. The links 12 may also incorporate shock absorbers or other damping devices for reducing vibrations.

Figure 2:
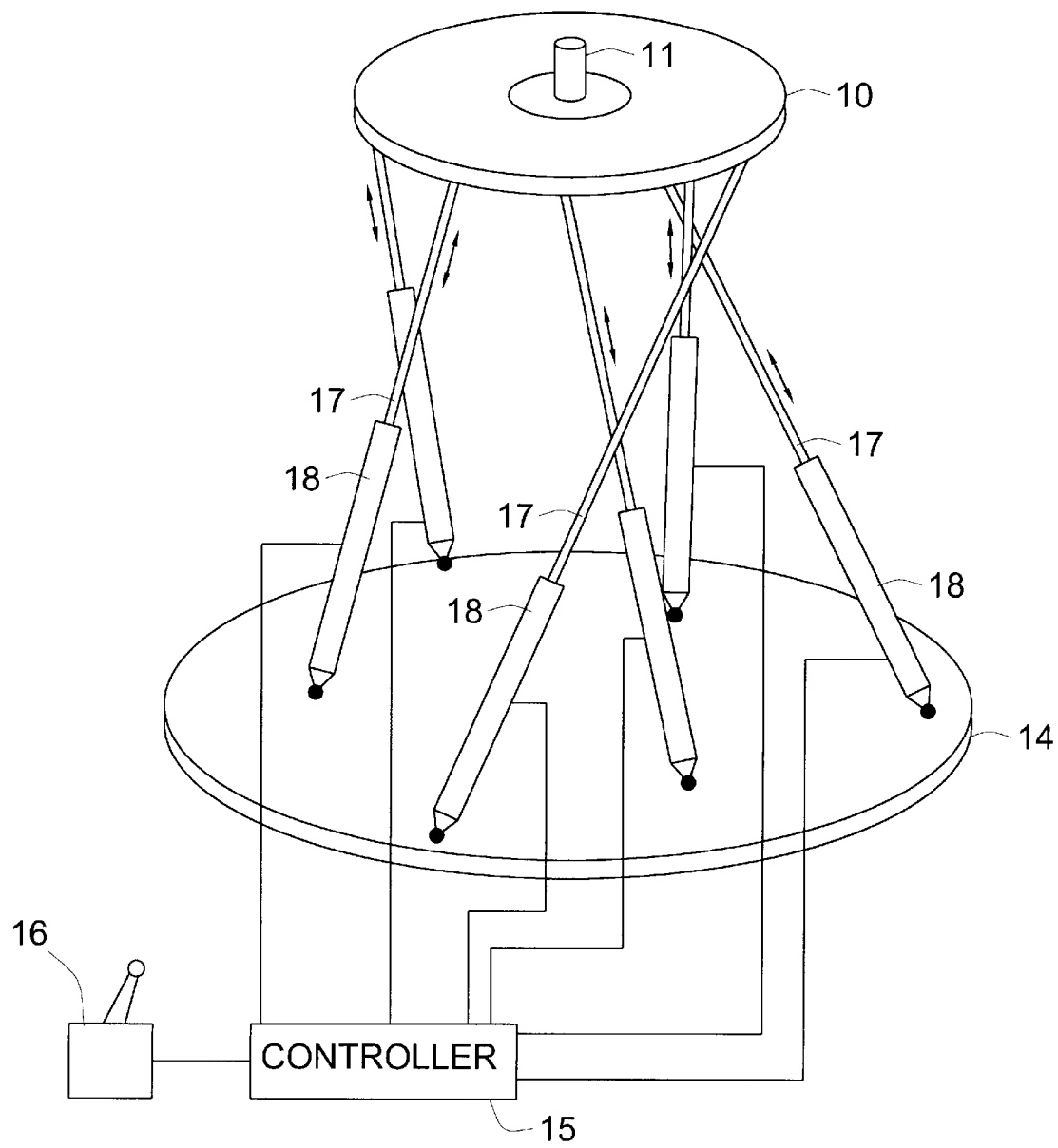
FIG. 2 schematically illustrates another embodiment of a parallel mechanism according to the present invention having variable-length active links.

FIG. 2 schematically illustrates another embodiment of a mechanism according to the present invention. This embodiment is similar to the embodiment of FIG. 1, but the passive links 12 of that embodiment have been replaced with what are referred to as active links 17, each of which has an actuator 18 associated with it, by means of which the link 17 can be adjusted in length to adjust the position of the end platform 10. The expression "associated with" includes both the situation in which the actuator 18 forms a part of the link 17 and the situation in which the actuator 18 is external to the link 17 but is operatively connected to the link 17 in a manner permitting adjustment of the length of the link 17. Each active link 17 has a first end pivotably connected to the end platform 10 and a second end pivotably connected to a support member 14, which may be stationary or movable like the support member 14 in the embodiment of FIG. 1. The operation of the actuators 18 to adjust the lengths of the links 17 is controlled by a controller 15 which is connected to the actuators 18 and which may operate autonomously or based on an input from a joy stick 16 or other suitable input device.

In the arrangements of both FIGS. 1 and 2, when the links are rigid members, the link geometry is such that the end platform 10 is kinematically restrained by the links, meaning that the position or orientation of the end platform 10 can be changed only by moving the second ends of the links (in the case of FIG. 1) or by changes in the lengths of the links (in the case of FIG. 2). In other words, simple rotation of the links about their second ends unaccompanied by translation of the second ends or changes in the lengths of the links will not changes the position or orientation of the end platform.

A parallel mechanism according to the present invention is not limited to having only active links or only passive links, and two types of links can be employed in a single mechanism. Furthermore, an active link may have its lower end movably supported, in which case it can function as a hybrid of an active link and a passive link.

Either an active link or a passive link may extend along a straight line between the two ends of the link, or a link may extend along a path which deviates from a straight line between its two ends. As described below, with some link geometries, the range of movement of the links before interference occurs between adjoining links can be significantly increased by giving the links a nonlinear shape, such as curved, crank-shaped, V-shaped, etc. For simplicity of structure and control, the links will generally be of the same length as each other, but it is also possible for the lengths to vary among the links.

A mechanism according to the present invention can have various numbers of links depending upon the number of degrees of freedom with which it is desired to manipulate the end platform. Typically, it will have six links so as to enable the end platform to be controlled with six degrees of freedom, but it may have fewer links if a lesser degree of control is desired. It is possible to have more than six links, although having a large number of links will typically increase the complexity of control and possibly reduce the range of movement of the end platform before the links interfere with each other.

Figure 3:
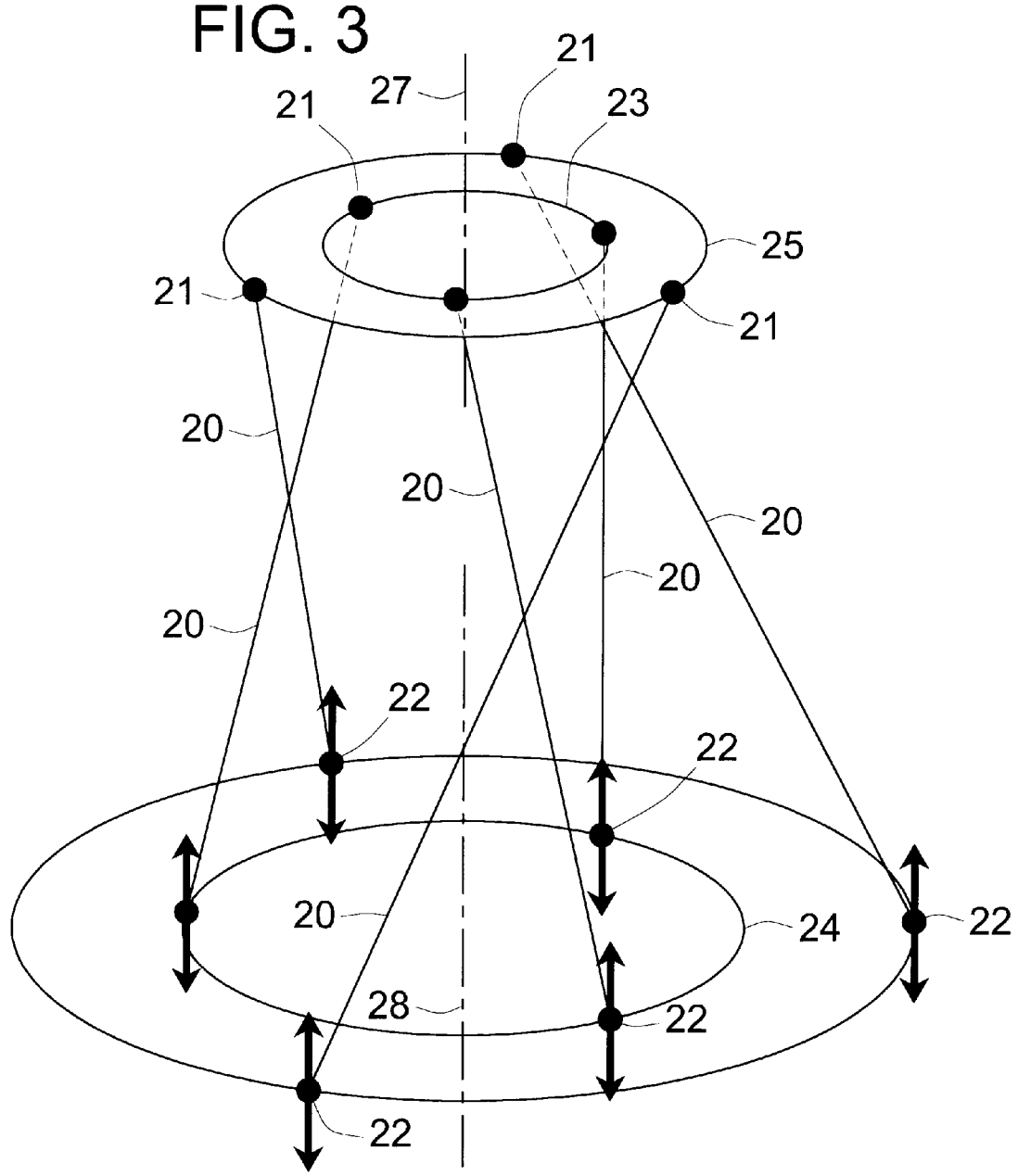
FIGS. 3–7 schematically illustrate various examples of link geometries in a parallel mechanism according to the present invention.
Figure 4:
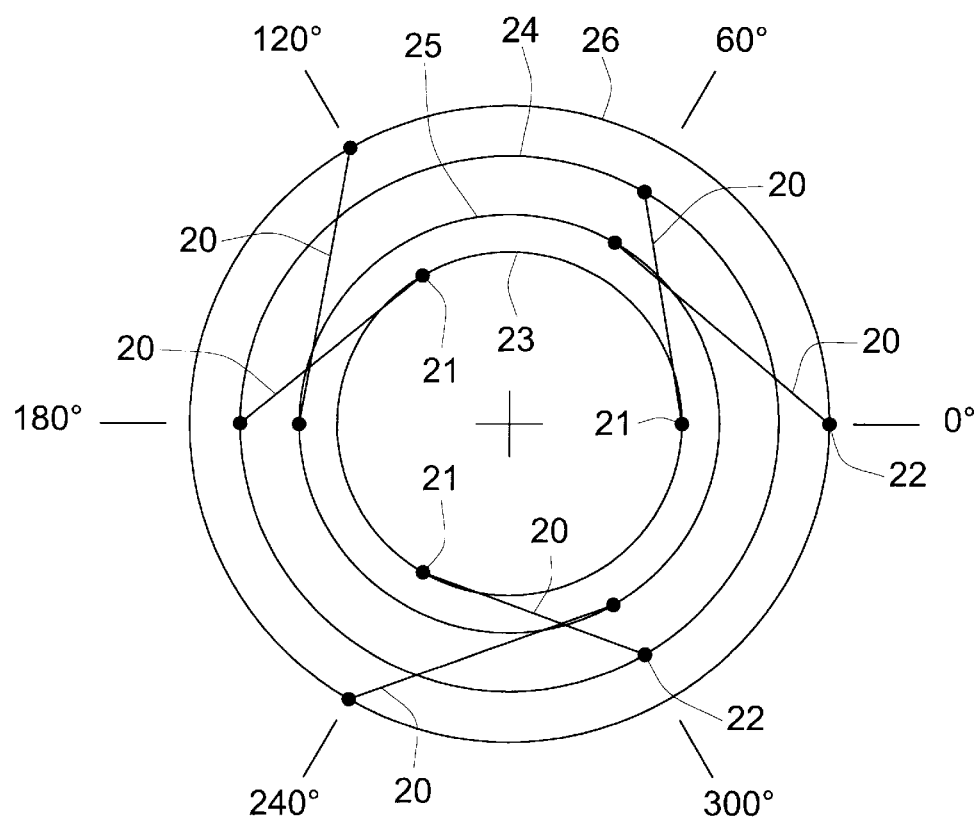
Figure 5:
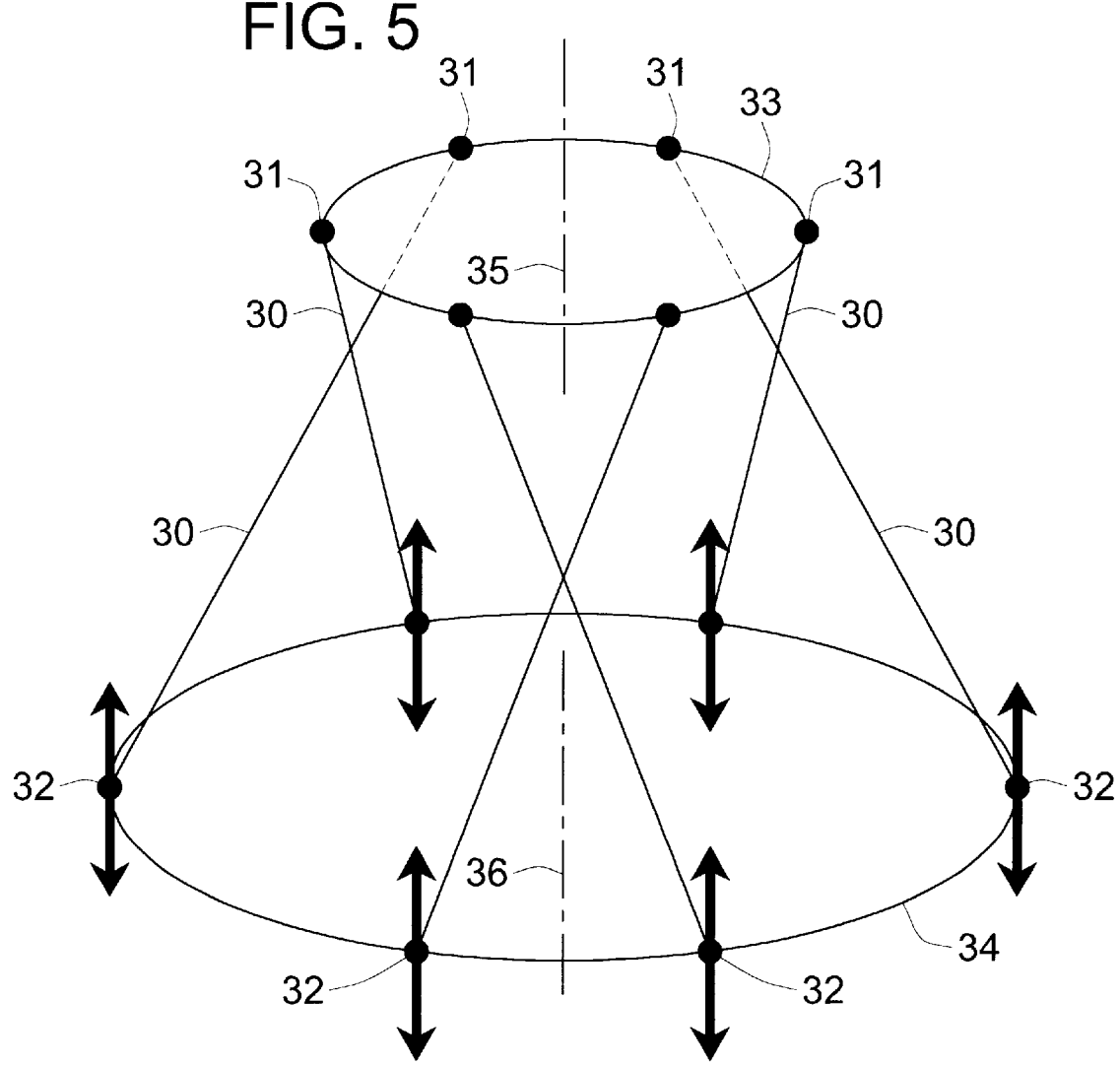
Figure 6:
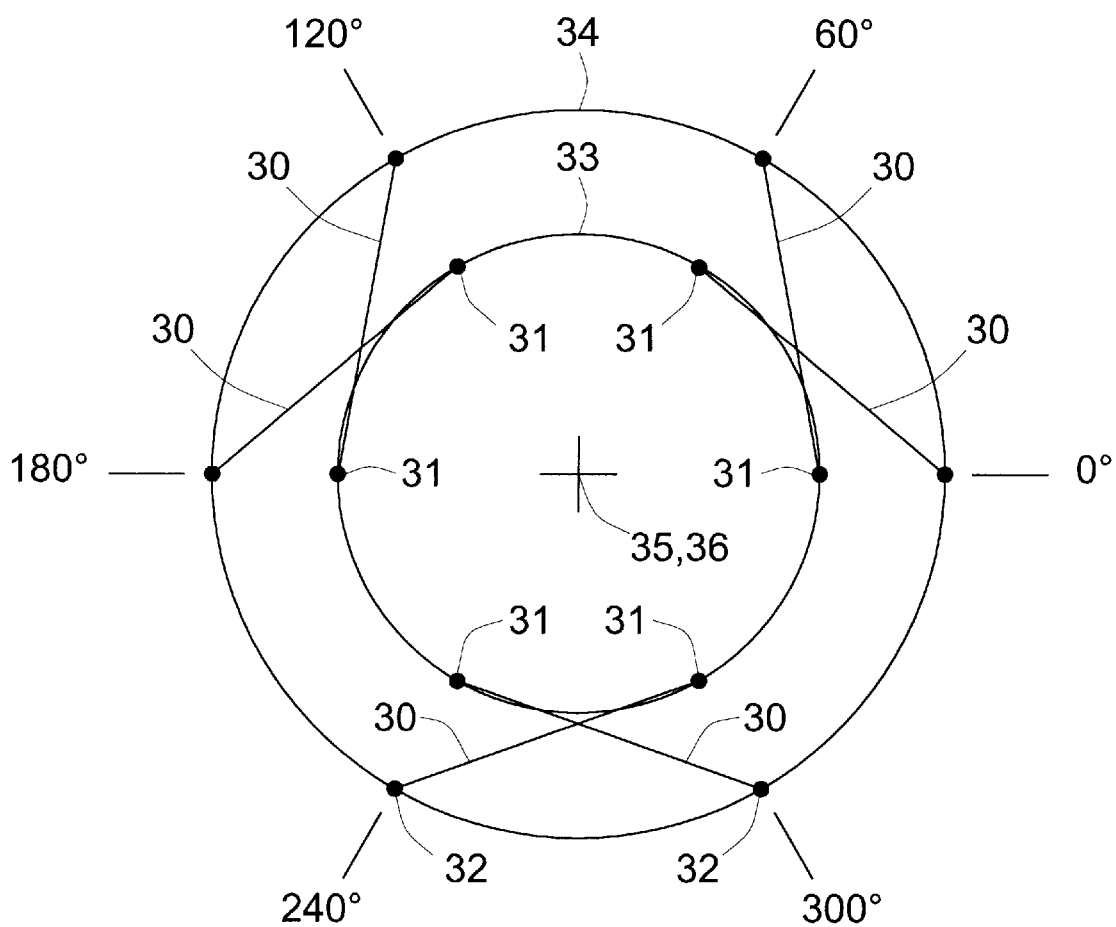
Figure 7:
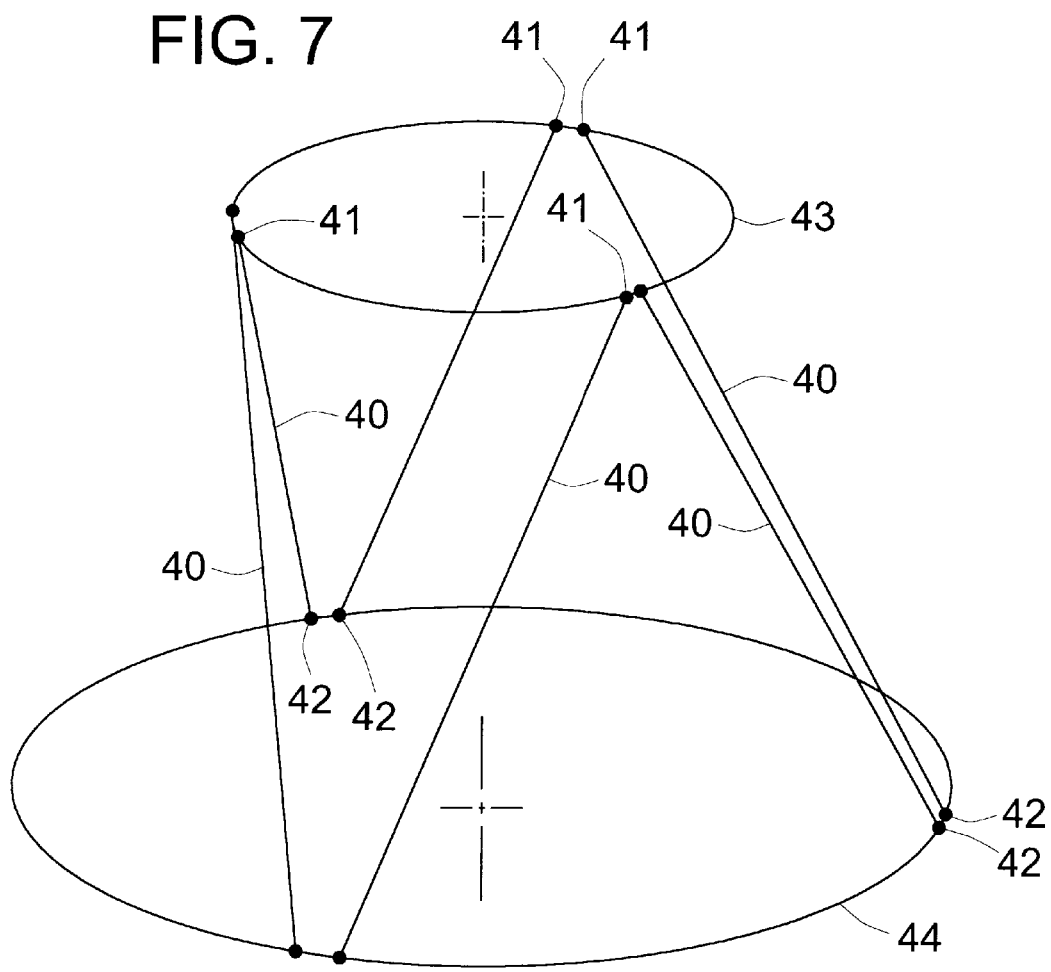

The links of a parallel mechanism according to the present invention can be arranged in a wide variety of geometries. Three examples of possible geometries which can be employed either with active links or passive links are shown in FIGS. 3–7. FIGS. 3, 5, and 7 are isometric views of the three different geometries, and FIGS. 4 and 6 are plan views of the geometries of FIGS. 3 and 5, respectively. Each figure represents a reference position of the mechanism with respect to which the upper ends of the links can be translated to change the position or orientation of an unillustrated end platform supported atop the upper ends of the links. The small circles at the ends of the links represent the centers of rotation of joints connecting the ends of the links to other members, such as an end platform, a support base, or an actuator. Each joint is assumed to have a single center of rotation, i.e., all axes of rotation of a given joint are assumed to intersect at a single point. For simplicity, each link is shown as a straight line extending between the joints at its two ends, but a link may instead extend non-linearly between the joints. While it will be assumed that the upper ends of the links in the figures are connected to the end platform which is to be manipulated, the end platform could instead be connected to the lower ends of the links.

In the reference position of the geometry shown in FIG. 3, the centers of rotation 21 of the joints at the upper ends of three links 20 are located on a first circle 23 having an axis 27, and the centers of rotation 22 of the joints at the lower ends of these links are located on a second circle 24 which has an axis 28 and which is coaxial with but spaced in the axial direction from the first circle 23. The centers of rotation 21 of the joints at the upper ends of three more links 20 are located on a third circle 25 coplanar and coaxial with the first circle 23, and the centers of rotation 22 of the joints at the lower ends of these links 20 are located on a fourth circle 26 coplanar and coaxial with the second circle 24. In this figure, the second circle 24 is larger than the first circle 23 and the fourth circle 26 is larger than the third circle 25 so that the links 20 are sloped inwards with respect to the axes 27 and 28 of the circles from circles 24 and 26 to circles 23 and 25, but the diameters of the circles can be selected so that the links are sloped in the opposite direction, i.e., the second circle 24 can be smaller than the first circle 23 and the fourth circle 26 can be smaller than the third circle 25. Alternatively, the diameters of the various circles can be selected such that some of the links 20 are sloped inwardly and the other links are sloped outwardly from circles 24 and 26 to circles 23 and 25. The centers of rotation 21 of the six joints on the first and third circles 23 and 25 are substantially equally spaced around the common axis 27 of these circles, i.e., they are located at angular intervals of approximately 60 degrees, and the centers of rotation 22 of the six joints on the second and fourth circles 24 and 26 are likewise substantially equally spaced around the common axis 28 of these circles. As shown in FIG. 4, which is a plan view of the mechanism illustrated in FIG. 3, the angular position of the center of rotation 21 of the upper joint of each link 20 with respect to the angular position of the center of rotation 22 of the lower joint of the same link 20 is such that when the mechanism is viewed along the aligned axes 27, 28 of the four circles 23–26, adjoining links 20 appear to intersect each other, although they do not actually intersect when the mechanism is in its reference position. Therefore, in FIG. 3, half of the links 20 have been drawn as broken lines to indicate that there is no intersection between the links 20. In the reference position, if the centers of rotation 22 of the joints at the lower ends of the links 20 are located on circles 24 and 26 at angles of approximately 0, 60, 120, 180, 240, and 300 degrees around the aligned axes 27, 28 of the circles (taking the position of the center of rotation 22 of an arbitrary one of the joints as 0 degrees), then the centers of rotation 21 of the joints at the upper ends of the same links 20 are located on circles 23 and 25 at approximately 60, 0, 180, 120, 300, and 240 degrees, respectively. The arrows passing through the centers of rotation of the lower joints of the links 20 in FIG. 3 illustrate examples of paths of movement for these joints when the links 20 are passive links rotatably connected to unillustrated actuators at their lower joints.

FIG. 5 is an isometric view of a link geometry in which, in the illustrated reference position, each of six links 30 of equal length has a joint at its upper end having a center of rotation 31 located on a first circle 33 and a joint at its lower end having a center of rotation 32 located on a second circle 34 coaxial with but spaced axially from the first circle 33, and FIG. 6 is a plan view of the geometry of FIG. 5. The centers of rotation 31 of the joints at the upper ends of the links 30 are substantially equally spaced, i.e., located at intervals of approximately 60 degrees around the axis 35 of the first circle 31, and the centers of rotation 32 of the joints at the lower ends are substantially equally spaced around the axis 36 of the second circle 34. This geometry is one which results by combining the first and third circles 23 and 25 in FIG. 3 with each other and by combining the second and fourth circles 24 and 26 of FIG. 3 with each other. When the mechanism is viewed along the aligned axes 35, 36 of the circles 33 and 34, as shown in FIG. 6, adjoining links 30 appear to intersect each other. As with the arrangement shown in FIGS. 3 and 4, in the reference position, the centers of rotation 32 of the joints at the lower ends of the links 30 are located at angles of approximately 0, 60, 120, 180, 240, and 300 degrees around the aligned axes 35 and 36 of the circles 33 and 34 (taking the position of the center of rotation 32 of an arbitrary one of the joints as 0 degrees), while the centers of rotation 31 of the joints at the upper ends of the same links 30 are located at approximately 60, 0, 180, 120, 300, and 240 degrees, respectively. In the reference position shown in FIG. 5, adjoining links 30 will actually intersect with each other if each link 30 extends along a straight line connecting the centers of rotation 31 and 32 of the joints at its upper and lower ends. Therefore, for the link geometry shown in FIG. 5. At least one-half of the links 30 (every other link) will have a shape deviating from a straight line to prevent interference between links 30 when the mechanism is in the reference position as well as to increase the range of movement in which no interference takes place.

The link geometry shown in FIG. 7 is that of a typical Stewart Platform in which the centers of rotation 41, 42 of the joints at the upper and lower ends, respectively, of six links 40 of equal length are grouped in three pairs on a first circle 43 and on a second circle 44 coaxial with and axially spaced from the first circle 43 when the mechanism is in a reference position. With this geometry, the links 40 do not appear to intersect each other when the mechanism is viewed along the aligned axes of the first and second circles 43 and 44.

Numerous other geometries are possible by modifying the above geometries. For example, the various upper and lower circles can have different axes; the centers of rotation of the joints at the upper ends of the links may lie on a single circle while the centers of rotation of the joints at the lower ends lie on multiple circles or vice versa; the centers of rotation of the joints at the ends of the links need not be evenly spaced around the respective circles; the centers of rotation of the joints at the upper or lower ends of the links need not lie in a single plane; and the links may be non-uniform in length.

Of the various geometries which can be employed, geometries in which the links appear to cross each other when the mechanism is viewed along the aligned axes of the upper and lower circles are preferred because, for circles of a given radius and separation, such geometries permit the links to be sloped at a greater angle to the axes of the circles than if the links do not appear to cross. As the angle of a link with respect to the axes of the circles increases, the greater is the force which can be exerted on an end platform by the upper end of the link in a direction perpendicular to the axes. With a typical Stewart platform geometry such as that shown in FIG. 7, the links 40 are at a fairly small angle with respect to the axes of the first and second circles 43 and 44, with the result that the force which can be exerted by the links in a direction parallel to the axes is much greater than the force which can be exerted by the links in a direction normal to the axes. With geometries such as those shown in FIGS. 3 through 6 in which the links appear to cross each other, the force which can be exerted in a direction normal to the axes is closer in magnitude to the force which can be exerted parallel to the axes, so a mechanism having one of these geometries has a greater dexterity.

Having the centers of rotation of the joints spaced substantially equally around an axis when the mechanism is in its reference position is advantageous because it permits a large work space by reducing interference between links. Even spacing of the centers of rotation of the joints also increases the stiffness of the mechanism as well as results in the most compact base for the mechanism when the actuators are placed as close to each other as possible.

Having the centers of rotation of all the upper joints on a single circle and having the centers of rotation of all the lower joints on another circle typically permits a large range of motion and results in a more even distribution of loads on the links, particularly when a torque is applied to the end platform.

As stated above, many of the link geometries which can be employed in the present invention may utilize either active or passive links. However, passive links frequently have a number of advantages over active links. Passive links can generally be smaller in diameter than active links, so a greater range of movement is possible before interference between adjoining links occurs. In addition, because passive links are much simpler in structure than active links, it is easier to miniaturize a mechanism employing passive links. Furthermore, it is easier to make passive links in a non-linear or other desired shape than to do so for the active links. Also, since a passive link typically has no moving parts, it can be designed to have a high stiffness more readily than an active link. In addition, since the actuators for passive links will generally be further from the end platform than the actuators for active links, it is easier to connect electrical wiring, hydraulic lines, or other members to the actuators for passive links than for active links. A particularly important advantage of passive links over active links is that the moving mass of a parallel mechanism with passive links can be much less than that of a parallel mechanism of the same size with active links. With an active link, the actuator is disposed between the two ends of the link, so the entire actuator undergoes movement every time the link is changed in length. In contrast, with a passive link, the actuator is outside of the link, and generally only a portion of the actuator undergoes movement as the link moves. As a result, the inertia of the parallel mechanism as a whole is much lower, enabling more rapid changes in direction of movement. A lower inertia also increases safety, permits more accurate control of force and position, and results in a higher mechanical bandwidth.

When the links are active links, the actuators will typically act along a linear path coinciding with a line connecting the two ends of the corresponding link. In the case of passive links, the actuators can act on the lower ends of the links in any direction which will produce a desired movement of the upper ends of the links. For simplicity, each actuator will typically act along a linear path parallel to a common axis (such as the axis of one of the lower circles in FIGS. 3–7), but the paths of movement of the actuators need not be parallel to each other. Linear actuators which act along a linear path are particularly suitable, but it is also possible to use non-linear actuators. A wide variety of actuators can be employed, such as linear electric motors, rotary motors connected to motion converting mechanisms (such as ball-bearing screws or racks and pinions) for converting rotary to linear motion, and hydraulic or pneumatic cylinders. When the end platform only needs to assume a small number of positions, an actuator having only a small number of discrete states, such as a solenoid, can be used, but when it is desired to manipulate the end platform with many degrees of freedom, such as six degrees of freedom, the actuators preferably permit substantially continuous position control. Among various types of actuators, linear electric motors are particularly suitable, especially for applications in which precise control of the end platform is desired.

In the past, parallel mechanisms have been powered either by hydraulic or pneumatic pistons connected to the links, or by rotary motors connected to a motion converting mechanism for converting the rotational movement of the motors into linear movement for driving the links. Linear electric motors have not been used as link actuators in parallel mechanisms. However, linear electric motors have a number of important yet hitherto unrecognized advantages over conventional actuators when employed in parallel mechanisms.

One advantage is that linear motors produce a linear output force, so they can be used to directly drive either an active link or a passive link of a parallel mechanism without the need for ball bearing screws or other motion converting mechanisms (which produce backlash, increased inertia, and increased friction, all of which are detrimental to precise control of a mechanism) to be disposed between the linear motors and the links. Thus, a parallel mechanism with linear motors as actuators can be controlled with extremely high precision.

Another advantage of using linear motors as actuators in a parallel mechanism is that the moving mass of a linear motor is essentially independent of the range of movement of the moving portion of the motor. In contrast, for most other types of actuators, including hydraulic cylinders or motors connected to ball bearing screws, an actuator with a long range of movement will tend to have a greater moving mass undergoing rotation and/or translation than an actuator with a short range of movement. Therefore, a parallel mechanism employing linear motors as actuators can have a long range of movement while still having a low moving mass and low inertia.

Still another advantage of linear motors is that they have very low friction, which is highly advantageous from the standpoint of achieving accurate force control and/or position control. This low friction results in linear motors being backdrivable, i.e., they can be driven by an external force exerted in the direction opposite to the direction of the force exerted by the motor.

The ends of each link are equipped with joints which enable each end to pivot with multiple degrees of freedom with respect to a member to which the link is connected (such as an end platform, a base, or an actuator) during the operation of the mechanism. Various types of rotatable joints can be used for this purpose, such as universal joints (Hooke's joints, etc.) or spherical joints (ball and socket joints, etc.). Preferably the joint at one end of each link enables the link to pivot with three degrees of freedom relative to the member to which the one end is connected, while the joint at the other end of the link enables the link to pivot with at least two degrees of freedom relative to the member to which the other end is connected. For example, the joint at one end can have three rotational degrees of freedom while the joint at the other end has two rotational degrees of freedom, or both joints can permit three rotational degrees of freedom. Calculation of the kinematics of the mechanism is simpler if each joint has a single center of rotation, i.e., if all of axes of rotation of the joint intersect at a single point, but the joints may also be of a type which does not have a single center of rotation.

Figure 8:
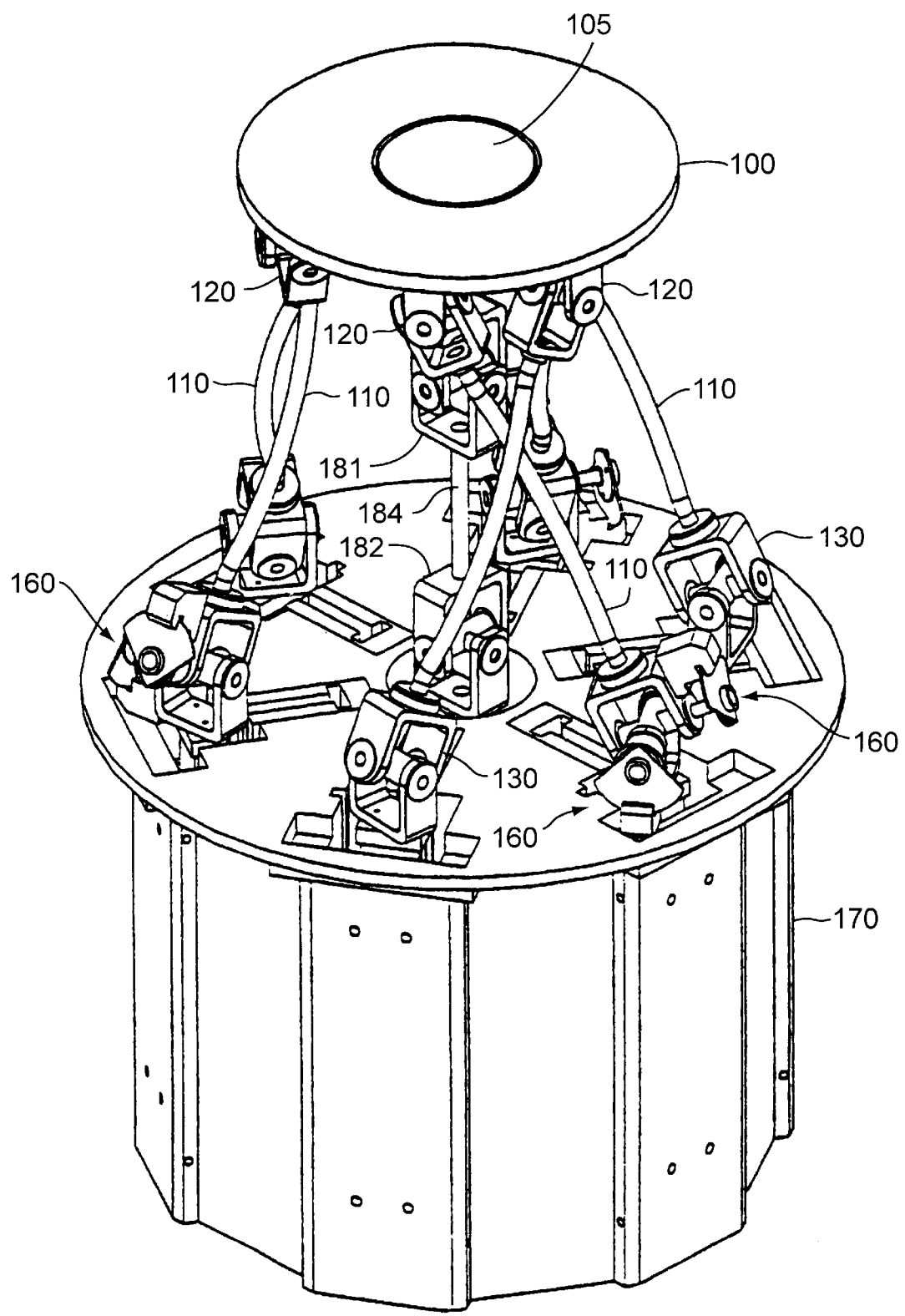
FIG. 8 is a more concrete isometric view of an embodiment of a parallel mechanism according to the present invention.
Figure 9:
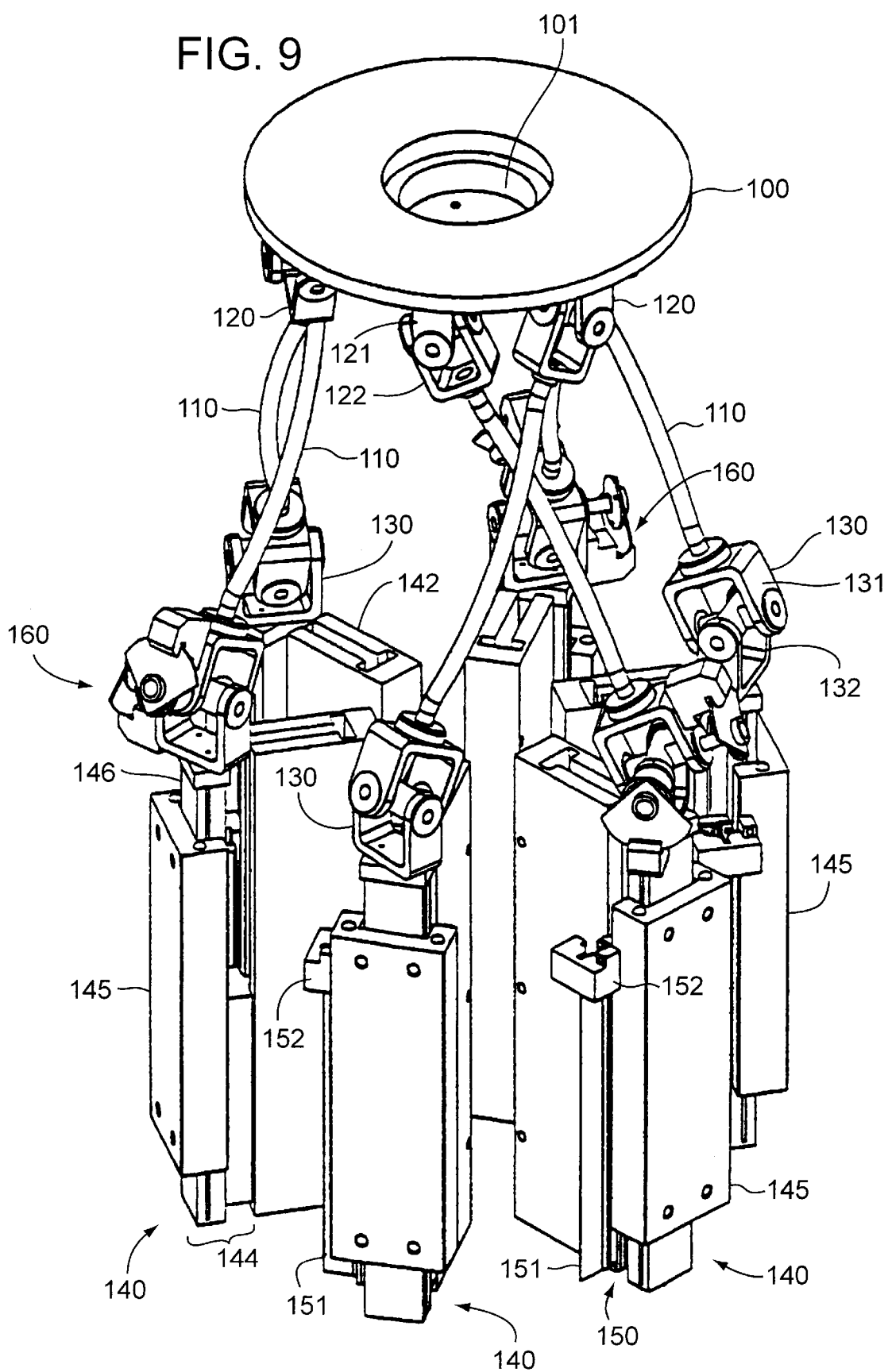
FIG. 9 is an isometric view of an embodiment of FIG. 8 with a base of the mechanism removed for clarity.

FIGS. 8–16 are more concrete illustrations of an embodiment of a parallel mechanism of the type shown in FIG. 1 employing passive links driven by linear actuators. FIG. 8 is an isometric view of the embodiment, and FIG. 9 is an isometric view of the same embodiment with a support base of the mechanism removed for clarity. The mechanism includes an end platform 100 for supporting a load, six curved links 110 supporting the end platform 100, and a linear actuator 140 comprising a linear motor 141 associated with each link 110. The mechanism also includes a base 170 for supporting the actuators 140 and for maintaining a desired spacing between them. The upper end of each link 110 is pivotably connected to the end platform 100 by an upper universal joint 120 having two axes of rotation, and the lower end of each link 110 is pivotably connected to one of the actuators 140 by another universal joint 130 having three axes of rotation. The links 110 are of equal length and identical shape and are arranged in the geometry shown in FIG. 5, with the centers of rotation of the upper joints 120 equally spaced around a first circle and with the centers of rotation of each of the lower joints 130 equally spaced around a second circle coaxial with and axially spaced from the first circle when the mechanism is in a reference position.

The end platform 100 in this embodiment is generally disk-shaped, but it can have any shape suited to the equipment which it needs to support or the shape of the space in which it is to be manipulated, such as polygonal or a combination of polygonal and curved shapes. While the illustrated end platform 100 has an upper surface which is substantially flat, it may be convex, concave, stepped, or otherwise deviate from a planar shape. The end platform 100 can be used to support a variety of tools, sensors, or other objects, depending upon the task which it is to perform, and its shape or other structural features can be selected in accordance with the nature of the object which is to be supported.

Figure 10:
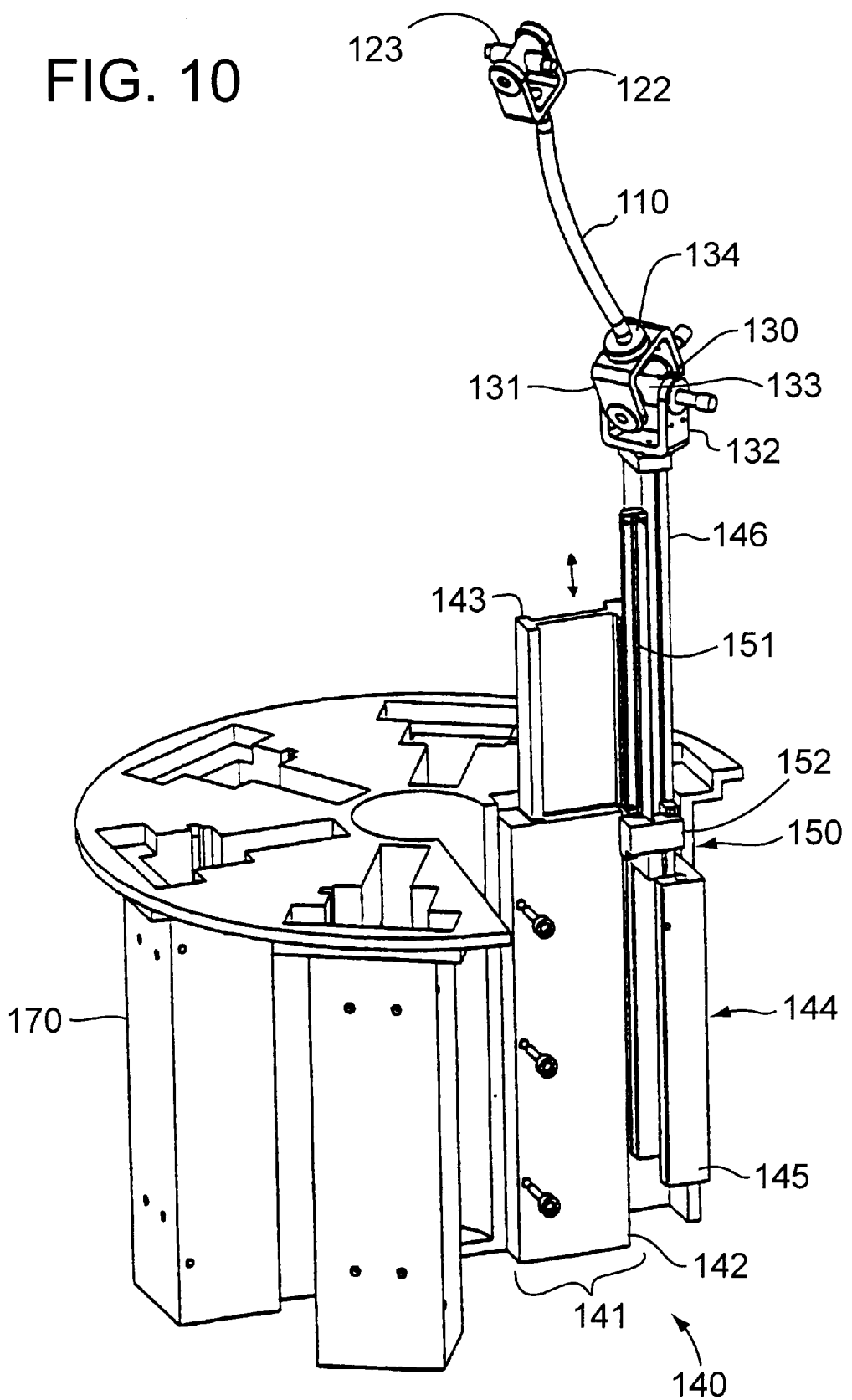
FIG. 10 is an isometric view of the base and one of the linear actuators of the embodiment of FIG. 8.

FIG. 10 is a detailed view of one of the linear actuators 140 and the corresponding link 110 which is driven by it.

Each actuator 140 includes a permanent magnet DC linear motor 141, such as those manufactured by Trilogy Systems of Webster. Texas, although many other varieties and brands of linear motors can be employed, such as AC vector drive linear motors. Of the various types of permanent magnet DC linear motors which exist, moving-coil motors are preferable to moving-magnet or moving-armature types because moving-coil motors provide a higher force-to-inertia ratio, although these other types may also be employed. The illustrated linear motors 141 are moving-coil motors including a magnet track 142 comprising a plurality of permanent magnets disposed in series, and a coil unit 143 comprising a set of coils wrapped on a nonmagnetic support bar made of aluminum, for example, and movably disposed in a slot of the magnet track 142 for linear movement in the lengthwise direction of the magnet track 142. In the present embodiment, the magnet track 142 is mounted on the base 170 of the mechanism. The magnet track 142 may have any desired length appropriate for the desired range of movement of the end platform 100. The coil unit 143 may be supported for linear movement solely by the magnet track 142, but depending upon the load which is to be applied to the coil unit 143 and the sturdiness of the linear motor 141, it may be desirable to support the coil unit 143 for movement by a linear guide exterior to the motor 141 in order to reduce the mechanical load on the motor and reduce play between the magnet track 142 and the coil unit 143. Therefore, in the present embodiment, the coil unit 143 is supported by a conventional linear guide 144, such as a ball slide having a stationary block 145 secured to the base 170 and a sliding bar 146 secured to the coil unit 143 and slidably supported by the block 145 for linear movement. A ball slide is particularly suitable as the linear guide 144 because it can have an extremely low coefficient of friction. Examples of suitable ball slides are those available from THK Co. Ltd. of Japan, which have a coefficient of friction on the order of 0.000125. As a result, the starting friction of the linear guide 144 is so low that the linear motor 141 (and therefore the lower joint 130 of the corresponding link 110) can be moved in extremely fine increments, resulting in its position being controllable with a high degree of precision. The upper end of the sliding bar 146 of the linear guide 144 is rigidly secured to the lower universal joint 130 of one of the links 110. The linear motors 141 in the present embodiment are controlled by digital sine wave commutation, although other types of motor control, such as pulse width modulation control, can instead be performed.

The current passing through the coil unit 143 may produce an increase in the temperature of the sliding bar 146 of the linear guide 144, resulting in its thermal expansion. To prevent the thermal expansion from decreasing tolerances and increasing the friction of the linear guide 144, the mechanism may be equipped with an unillustrated temperature controller which senses the temperature of the sliding bar 146 and the block 145 and heats the block 145 of the linear guide 144 with a heating coil or similar member associated with the block 145 so that the temperature of the block 145 is made to match that of the sliding bar 146, thereby preventing temperature gradients and uneven thermal expansion.

Figure 11:
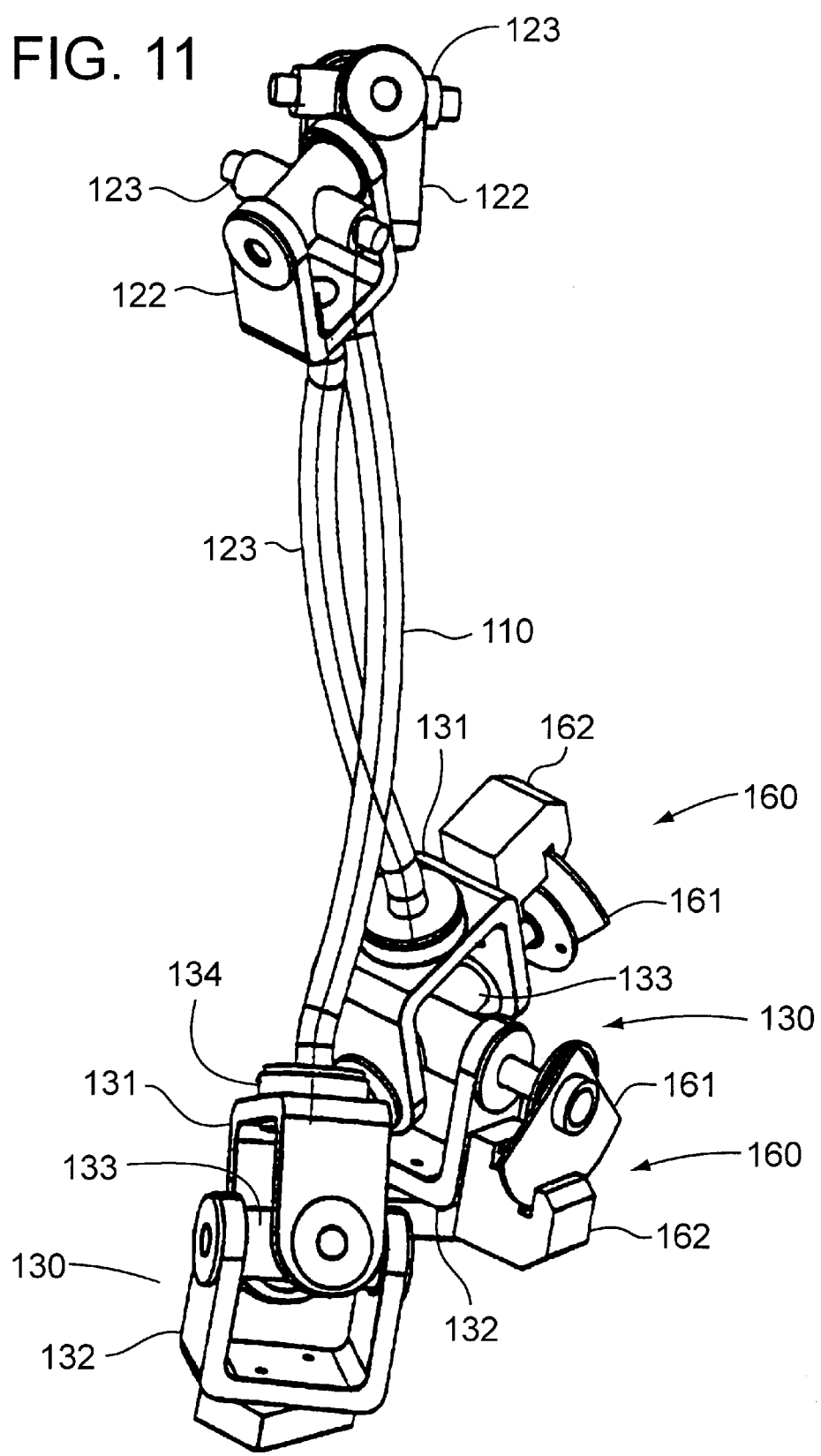
FIG. 11 is an isometric view of two of the links of the embodiment of FIG. 8.

FIG. 11 illustrates two adjoining links 110 of the embodiment of FIG. 8. Each link 110 is curved away from a straight line connecting the centers of rotation of the two joints 120, 130 at its ends to increase the range of movement of the links 110 without interference between adjoining links 110. One of the links 110 is bowed outwardly with respect to the central axis of the mechanism and the other link 110 is bowed inwardly, but the direction in which the links 110 are curved and the amount of curvature are not restricted to those shown in the illustrated arrangements and can be selected based on factors such as the desired strength of the links 110 and geometric constraints on the particular design. Up to a certain degree, the greater the eccentricity of the links (equal to the maximum deviation of the centerline of a link from a straight line connecting the two ends of the link), the greater the amount of movement of the links which is possible before adjoining links interfere with each other, although if the eccentricity of a link is too great, the link may interfere with other parts of the mechanism or with objects on the exterior of the mechanism. On the other hand, the bending moment which is applied to a link under a given load will generally increase as the eccentricity increases, possibly requiring an increase in the cross-sectional dimensions and the unit weight of the link in order for the link to withstand the increased bending moment. Thus, a suitable eccentricity of the links will depend upon the parameters (such as the permissible amount of movement without interference or the desired weight of the mechanism) which the designer wishes to optimize. An example of a suitable eccentricity is on the order of 10%.

When the mechanism is to be used for high precision manipulation, such as in surgery, in high precision machining, or in the assembly of fine manufactured parts, the links 110 are preferably as stiff as possible to give the mechanism a high resonant frequency and a high mechanical bandwidth. At the same time, the links 110 are preferably as light as possible to give the mechanism a very low inertia. Thus, for such applications, materials having a high ratio of stiffness to density are particularly suitable for use in forming the links 110. One example of such a material is AlBeMet, which is a trademark for a powder metal material including powders of aluminum and beryllium. AlBeMet is available from Brush Wellman of Elmore, Ohio. AlBeMet has a density on the order of 0.08 lb/in$^3$ and a Young's modulus on the order of $30 \times 10^6$ psi, (giving it an excellent stiffness to density ratio. It is also non-brittle, isotropic, and machinable. Other examples of materials which are suitable when a high stiffness to density ratio is desired for the links 110 are carbon fiber composites. However, the links 110 are by no means restricted to being formed of these materials and can be selected based on the physical properties desired for the particular application.

Figure 12:
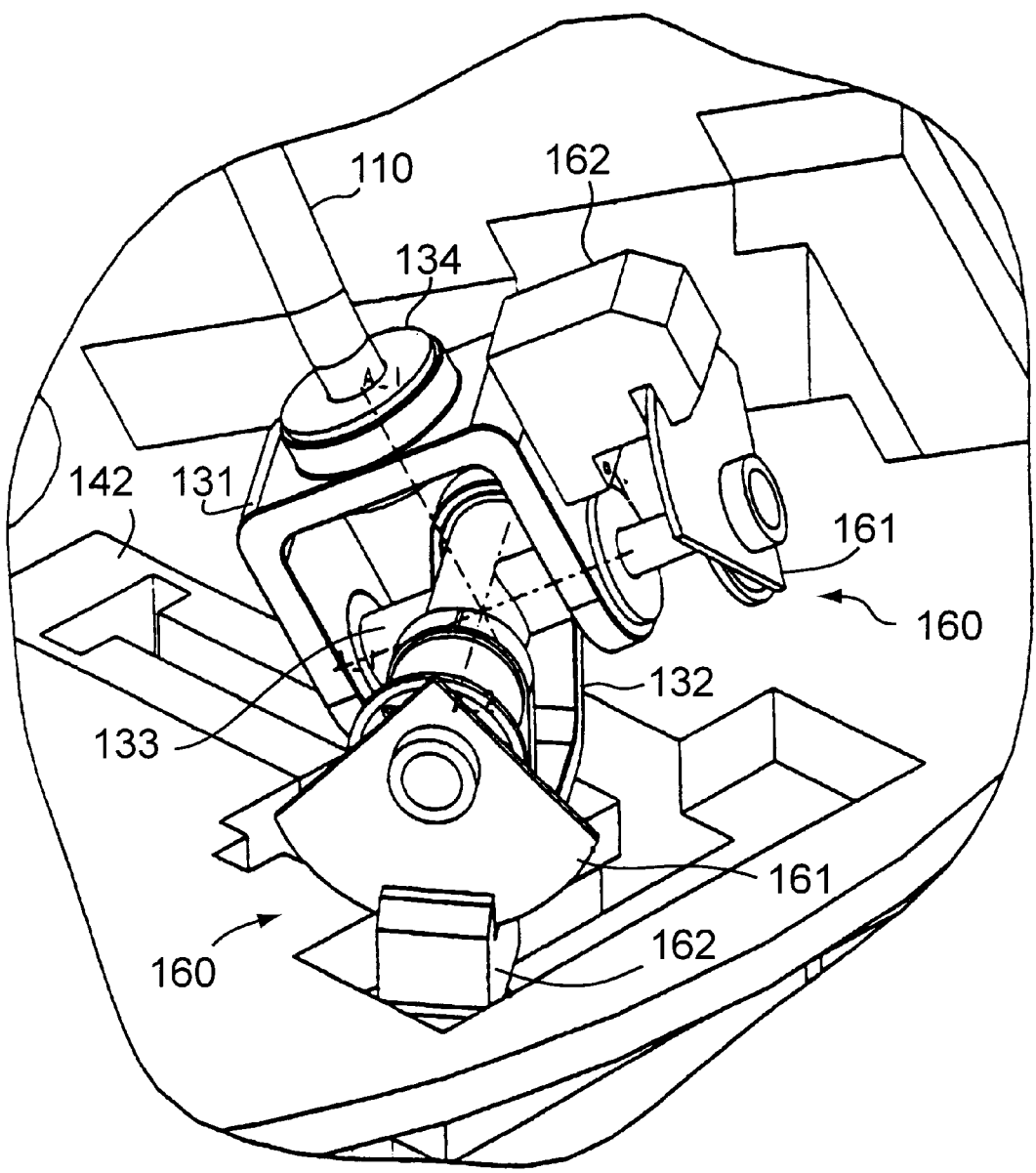
FIG. 12 is an enlarged isometric view of the lower joint of one of the links of the embodiment of FIG. 8.

FIG. 12 shows in detail the universal joint 130 connecting the lower end of one of the links 110 to a moving portion of one of the actuators 140. It includes an upper yoke 131 rotatably connected by one or more bearings 134 (such as a pair of preloaded bearings) to the lower end of the link 110, and a lower yoke 132 secured to the moving portion of the actuator 140. The two yokes 131 and 132 are each rotatably connected to an end of a cross piece 133 having two orthogonal axes about which the yokes can pivot. Each lower universal joint 130 therefore has three axes of rotation. For simplicity of calculating the kinematics of the mechanism, the two axes of rotation of the yokes 131 and 132 about the cross piece 133 preferably intersect each other, and more preferably all three axes of rotation intersect at a single point, as in the present embodiment. However, it is also possible for the axes to be non-coincident.

The joint 120 connecting the upper end of the link 110 to the end platform 100 is similar in structure to the joint 130 for the lower end and includes an upper yoke 121 and a lower yoke 122, each rotatably connected to a cross piece 123 having two orthogonal axes of rotation. For simplicity of calculating the kinematics of the mechanism, the two axes of rotation are preferably intersecting. The lower yoke 122 is rigidly secured to the upper end of the link 110, while the upper yoke 121 is rigidly secured to the end platform 100. As a result, the upper joint 120 provides only two rotational degrees of freedom. However, by rotatably connecting one of the yokes 121, 122 to either the link 110 or the end platform 100, the upper joint 120 may provide three rotational degrees of freedom. In order to increase the stiffness of the mechanism, the upper yokes 121 may be integrally formed with the end platform 100 if desired.

The kinematics of the mechanism are simpler to compute if the axis of rotation of the link 110 with respect to the upper yoke 131 of the lower joint 130 coincides with a straight line connecting the center of rotation of the upper joint 120 and the center of rotation of the lower joint 130, but this axis may be non-coincident with this line.

In order to calculate the position of the end platform 100 at any time, it is desirable to know the position of the lower end of each link 110. The position of the lower end of the link 110 can be sensed directly, but it is generally easier to sense the position of a member connected to the link, such as the moving portion of the linear actuator 140 associated with the link 110. The position of the actuator 140 can be sensed by a wide variety of conventional sensing mechanisms which sense the movement or the position mechanically, magnetically, optically, or in another manner, including potentiometers, linearly variably differential transformers, optical encoders, and Hall effect sensors. When fine control of the position of the end platform 100 is desired, a holographic interferometric linear encoder is particularly suitable for use as a position sensor because it can sense absolute position with a resolution of as fine as 10 nanometers. Such absolute linear position sensors 150 are employed in the present embodiment. Each position sensor 150, which is manufactured by MicroE Inc. of Natick, Mass., includes a position scale 151 secured to a moving portion of the actuator 140, such as the sliding bar 146 of the linear guide 144, and a position reader 152 mounted on a stationary portion of the mechanism, such as the base 170, with the position scale 151 movably disposed in a slot of the position reader 152. The position reader 152 generates an electrical output signal which indicates the location of the position scale 151 and which is provided to an electronic controller.

Three of the lower universal joints 130 are equipped with two rotational position sensors 160 for sensing the rotational position of a corresponding link 110 about two orthogonal axes. Like the linear position sensors 150 for the linear actuators 140, the rotational position sensors 160 may have any structure and operate based upon any physical principle. Holographic interferometric encoders similar to those used for the linear position sensors 150 for the linear actuators 140 are particularly suitable when a high resolution of position sensing is desired. The illustrated sensors 160 are holographic interferometric encoders manufactured by MicroE Inc. and include an arcuate position scale 161 and a position reader 162 having a slot in which the position scale 161 is movably disposed. The position reader 162 provides the electronic controller with an output signal indicative of the absolute rotational position of the position scale 161 and thus indicative of the angle of the link 110 about one of the axes of rotation of the lower joint 130. Each position reader 162 is secured to one of the yokes 131, 132 of the universal joint 130, while the position scale 161 is secured to one leg of the cross piece 133 on which the two yokes 131 and 132 of the universal joint 130 are rotatably mounted so that each position scale 161 is capable of rotational movement relative to the corresponding position reader 162.

Figure 15:
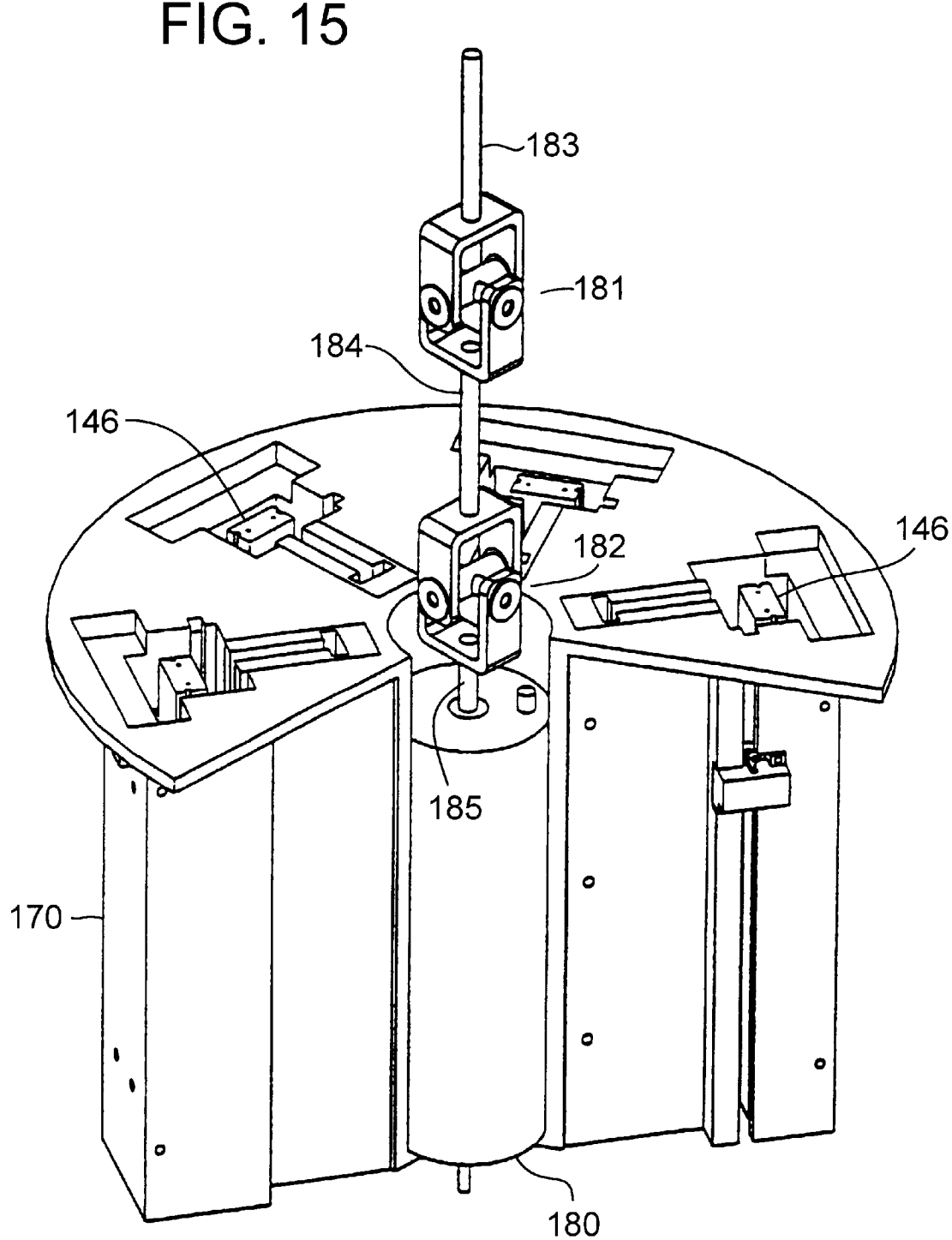
FIG. 15 is an isometric view showing a rotary actuator of the embodiment of FIG. 8.

By suitably controlling the movement of the links 110, it is possible to rotate the end platform 100 about an axis passing through and perpendicular to the plane of the end platform 100 while otherwise maintaining the orientation of the end platform 100 constant. However, the amount of rotation of the end platform 100 which is achievable in this manner before adjoining links 110 interfere with each other to prevent further rotation is limited, and there may be situations in which is it desired to rotate the tool or other object mounted on the end platform 100 by a greater number of degrees than is possible by translation of the links 110. To permit a greater amount of rotation, the end platform 100 may be equipped with a rotatable support member such as a rotatable tool plate 105 on which an object can be mounted and which can be continuously rotated with respect to the end platform 100 to provide any desired degree of rotation of the object. A drive mechanism for rotating the tool plate 105 can be mounted on the end platform 100 itself, but in order to minimize the weight of structures mounted on the end platform 100 so as to improve the responsiveness and controllability of the mechanism, in the present embodiment, the tool plate 105 is rotated by a motor 180 of any suitable type (such as a brushless, slotless DC motor) mounted on the base 170 and connected to the tool plate 105 in a manner which permits the motor 180 to transmit drive torque to the tool plate 105 at any orientation and location of the end platform 100 with respect to the motor 180. As shown in FIG. 15, two universal joints 181 and 182 drivingly connected to each other by a shaft 184 are disposed between the motor 180 and the tool plate 105. The upper yoke of the upper universal joint 181 is secured to a shaft 183 which is drivingly connected to the tool plate 105, while the lower yoke of the lower universal joint 182 is connected to the rotor of the motor 180 in a manner which permits the lower universal joint 182 and the rotor to undergo relative movement in the axial direction of the motor 180 while preventing them from rotating with respect to each other so that torque can be transmitted by the motor 180 to the lower universal joint 182. In the present embodiment, the lower universal joint 182 is connected to the motor 180 by a ball spline, but any other suitable type of connecting member for transmitting torque while permitting axial movement can be employed. The ball spline includes a spline shaft 185 secured to the lower yoke of the lower universal joint 182 and an unillustrated ball nut which is slidably mounted on the spline shaft 185 and secured to the rotor of the motor 180 so as to rotate with it. The rotor of the motor 180 is hollow, so the spline shaft 185 can pass through the center of the rotor as the spline shaft 185 slides up and down with respect to the ball nut. Examples of suitable ball splines are those available from THK Co. Ltd. As the end platform 100 is moved towards and away from the base 170 by operation of the linear actuators 140, the lower universal joint 182 can undergo axial movement relative to the motor 180 so that the motor 180 can rotate the tool plate 105 at varying distances of the tool plate 105 from the base 170. Furthermore, the universal joints 181 and 182 enable the tool plate 105 to be rotated by the motor 180 in any orientation of the end platform 100 with respect to the base 170. By suitably controlling the motor 180, the tool plate 105 can be rotated at speeds ranging from a few rpm or less when the tool plate 105 is used for slow positioning of an object up to thousands of rpm when the tool plate 105 is used for machining or other tasks involving high speed rotation.

FIGS. 13 and 14 are respectively an exploded isometric view and a vertical cross-sectional view showing the structure of the end platform 100 and the tool plate 105 which is rotatably supported by the end platform 100. For compactness, the tool plate 105 may be recessed in a cavity 101 of the end platform 100 to reduce its overall height. For example, the upper surface of the tool plate 105 may be substantially flush with the upper surface of the end platform 100. The tool plate 105 may be located anywhere on the end platform 100 and may be rotatably supported by the end platform 100 in any suitable manner. In the present embodiment, its axis of rotation coincides with the axis of the circle on which the centers of rotation of the upper joints 120 of the links 110 are located, and the tool plate 105 is rotatably supported by a pair of cross roller bearings 106 which may be preloaded to reduce play.

The mechanism may be equipped with one or more force sensors for sensing external forces acting on the end platform 100 so that the motions of the end platform 100 can be controlled in accordance with the sensed forces. Force sensors can be disposed in a variety of locations on the mechanism, with the end platform 100 being a particularly suitable location since there the sensors can directly sense the applied forces. In the present embodiment, a six degree of freedom force-torque transducer 108 is mounted on the end platform 100 in the cavity 101 beneath the tool plate 105. The lower surface of the transducer 108 is secured to the bottom of the cavity 101, and the upper surface of the transducer 108 is secured to a support plate 107 on which the two cross roller bearings 106 are mounted. The transducer 108 can sense axial force along three orthogonal axes and moments about these three axes and generate corresponding output signals, which are provided to the electronic controller. The transducer 108 which may be of any desired type. An example of a suitable force-torque transducer is a semiconductor strain gauge-type available from ATI Industrial Automation of Garner, N.C. The transducer 108 has a central bore through which the shaft 183 for connecting the tool plate 105 to the upper universal joint 181 can pass.

The tool plate 105 may be equipped with suitable structure, such as screw holes, brackets, or a chuck, by means of which a tool or other object can be secured to the tool plate 105. The portion of the end platform 100 surrounding the tool plate 105 may be equipped with similar structure for supporting various objects.

If desired, the tool plate 105 may be omitted, and a tool or other object which is to be rotated by the motor 180 may be connected directly to the shafting extending from the motor 180. In this case, all or a portion of the object can be disposed in the cavity 101 in the end platform 100, with only a portion of the object extending above the top surface of end platform 100, thereby decreasing the overall height of the mechanism. If the shafts connecting the tool plate 105 and the motor 180 are hollow, electrical wiring, fluid conduits, cables, fibers, or other members can conveniently pass through the shafts between the tool plate 105 and the base 170.

An example of a situation in which a rotatable tool plate 105 is particularly useful is when a parallel mechanism according to the present invention is used for machining. A workpiece to be machined can be mounted atop the tool plate 105 and rotated with respect to a tool supported by another member, or a tool can be mounted on the tool plate 105 and rotated with respect to a workpiece supported by another member. Machining of highly complex shapes can be performed if a workpiece is supported atop one parallel mechanism according to the present invention while a cutting tool is supported atop the tool plate 105 of another parallel mechanism according to the present invention.

Although the tool plate 105 is capable of being rotated independently of the end platform 100, there may be circumstances when it is desired to rotate the end platform 100 and the tool plate 105 as a unit, since the links 110 may be capable of exerting a higher torque on the end platform 100 than the motor 180 for the tool plate 105. Therefore, the tool plate 105 may be equipped with a locking mechanism, such as an electric brake, which can releasably lock the tool plate 105 to the end platform 100 when desired.

The tool plate 105 can be used to rotate a tool or other object in space about its axis, but it can also be used to restrain an object against rotation when the end platform 100 is being rotated in space. As stated above, the links 110 are capable of rotating the end platform 100 about an axis normal to the end platform 100, but after a certain amount of rotation, adjoining links 110 will interfere with each other, preventing further rotation. When the end platform 100 is equipped with a tool plate 105, after the end platform 100 has been rotated in a first direction by the links 110 to the point where adjoining links interfere, the motor 180, in its off state, can be used to maintain the tool stationary while the end platform 100 is rotated backwards in a second direction by the links 110 to "untwist" the links 110 from each other so that they no longer interfere. When the end platform 100 has been rotated backwards by a desired amount, the tool plate 105 can then be locked to the end platform 100, and the end platform 100 and the tool plate 105 can again be rotated as a unit in the first direction by operation of the links 110 to rotate the object.

One of the tool plate 105 and the end platform 100 can also be used to support an object while the other of the two applies a torque to the object or to another object engaged with the first object. For example, a nut could be grasped by a tool on the tool plate 105, a bolt could be grasped by another tool on the end platform 100, and the tool plate 105 could then be rotated with respect to the end platform 100 to screw the nut onto the bolt. Using the tool plate 105 and the end platform 100 in conjunction with each other in this manner to apply a torque to one or more objects is convenient in an environment, such as in outer space or underwater, in which it may be impossible to immobilize the base 170 which supports the actuators 140 against rotational movement.

Figure 16:
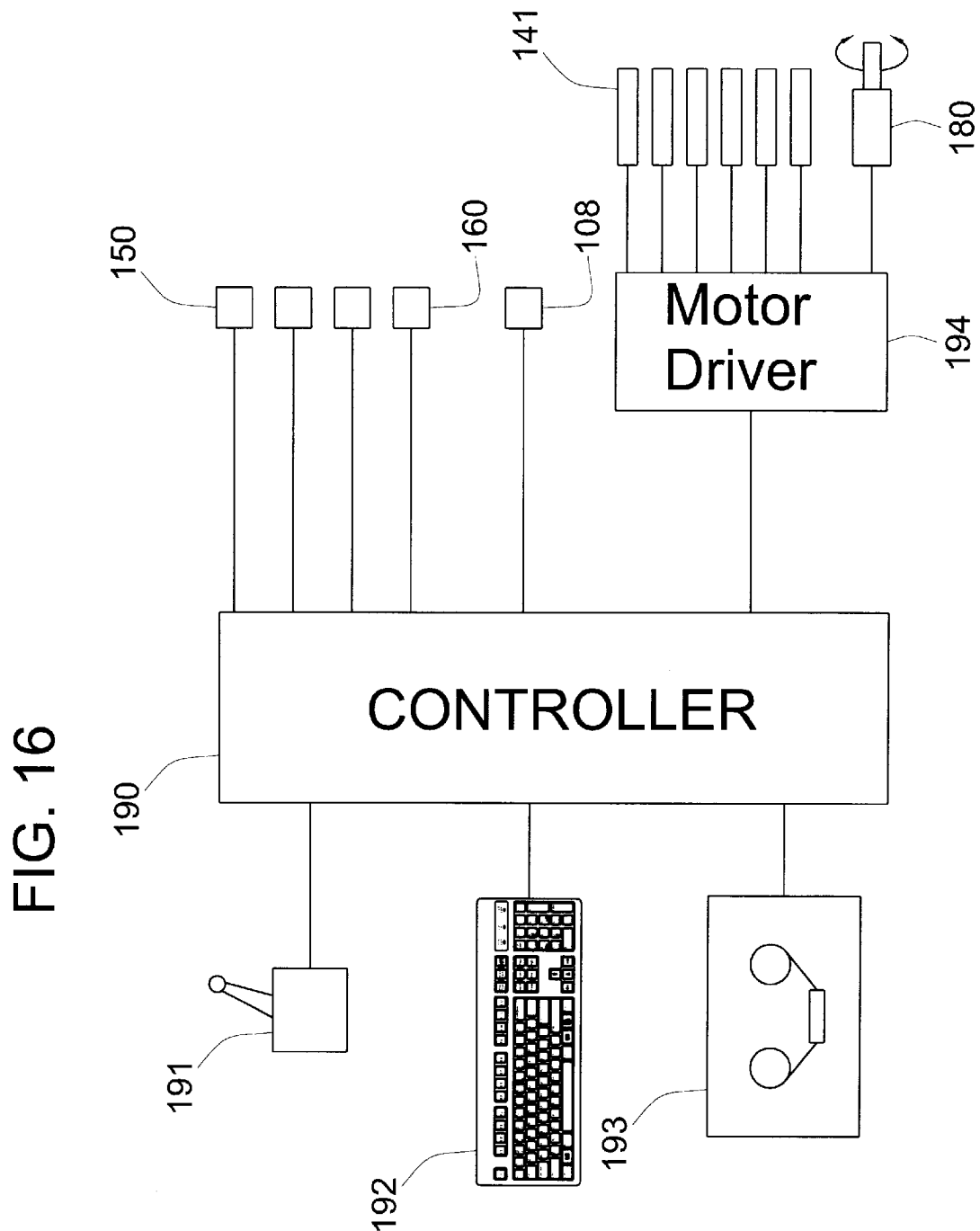
FIG. 16 is a block diagram of an example of a control system for the embodiment of FIG. 8.

A parallel mechanism according to the present invention will typically be equipped with a control unit, such as an electronic controller, for translating instructions from an input device into suitable commands for the linear motors. FIG. 16 illustrates an example of a control system which can be employed in the present invention. It includes an electronic controller 190 of any suitable type, such as a general purpose computer or a special purpose computer with one or more digital signal processors. The controller 190 receives input signals from the linear position sensors 150 for the linear motors 141, the rotational position sensors 160 for the lower joints 130 of the links 110, the force-torque transducer 108 for the tool plate 105, and any other sensors for sensing some operating parameter of the mechanism, such as a camera for forming an image of the end platform 100 or the work space in which the end platform 100 is operating. The controller 190 also receives input signals from one or more suitable input devices by means of which an operator can input the desired movement of the end platform 100. Some examples of possible input devices are a joy stick 191, a keyboard 192, a tape memory 193 or other data storage device which stores instructions for the movement of the end platform 100, a foot pedal, a mouse, a digitizer, a computer glove, or a voice operated controller. Based on the input from the input devices 191–193 and the signals from the position sensors 150 and 160 and the force/torque transducer 108, the controller 190 calculates or otherwise determines in real time the position of the end platform 100 and the motion of the individual links 110 required to move the end platform 100 in the desired manner. The controller 190 then provides suitable control signals to a motor driver 194 which amplifies the control signals using linear transconductance amplifiers, for example, and drives the appropriate linear motors 141 or the motor 180 for rotating the tool plate 105 to achieve the desired movement of the end platform 100. Linear transconductance amplifiers reduce force-torque ripple compared to pulse-width modulation amplifiers when used with digital sine wave commutation, but any suitable type of amplifier may be employed.

The controller 190 can control the mechanism in a variety of manners, depending upon the requirements of the task which is to be performed by the mechanism. For example, the controller 190 may perform position control, force control, or a combination of position and force control (hybrid position/force control) of the mechanism. Examples of these and other suitable control methods capable of use in the present invention and algorithms for their implementation are well known in the field of robotics and described in detail in published literature.

When the axes of the linear actuators 140 are parallel to each other and it is desired to move the end platform 100 along a straight line parallel to the axes, it is not necessary to know the position of the end platform 100 with respect to the base 170 in order to control the movement of the end platform 100, since the desired linear movement of the end platform 100 can be achieved by advancing or retracting the moving portions of all the linear actuators 140 by the same amount. However, if it is desired to move the end platform 100 in any other direction, or if the axes of the actuators 140 are not parallel to each other, it is generally necessary to know the position of the end platform 100 with respect to the base 170 in order to calculate the amount of movement of the actuators 140 required to move the end platform 100 in the desired direction. The position of the end platform 100 relative to the base 170 can be determined in a variety of ways. One way is to calculate the positions of the upper ends of the links 110 relative to the base 170 supporting the lower ends of the links 110 based on some combination of the lengths of one or more of the links 110, the positions of the lower ends of one or more of the links 110, the angular orientations of one or more of the links 110 with respect to the base 170, and the angular orientations of one or more of the links 110 with respect to the end platform 100. For passive links, the lengths of the links will usually be constant and so will be known in advance. For active links, the length of each link can be calculated with respect to an initial length as the link is shortened or elongated by operation of the actuator forming part of the link. When the lower ends of the links are movable, the positions of the lower ends can be sensed directly or can be determined by sensing the translation of the linear actuator associated with the lower end of each link with respect to a reference position. The angular orientation of the links 110 relative to the base 170 or the end platform 100 can be sensed by installing rotational position sensors on the joints at the lower or upper ends of one or more of the links 110. It is preferable to have any rotational position sensors installed on the lower joints 130 rather than on the upper joints 120 in order to reduce the moment of inertia of the mechanism measured from the base 170 so as to increase the responsiveness of the mechanism as well as to reduce the length of electrical wiring required for connecting the rotational position sensors to a controller. As described above, the embodiment of FIG. 8 employs six rotational position sensors 160, with two of the sensors 160 mounted on the lower joint 130 of each of three of the links 110. If the axis of rotation of each of these three links 110 in the corresponding bearing(s) 134 coincides with the center of rotation of the cross piece 133 of the lower joint 130 to which the link 110 is connected, the angles sensed by the two rotational position sensors 160 on the lower joint 130 define the position of the center of rotation of the upper joint 120 of the link 110 relative to the position of the center of rotation of the lower joint 130. Since the positions of the centers of rotation of the lower joints 130 for these links 110 relative to the base 170 are known from the output signals from the corresponding linear position sensors 150, then the positions of the centers of rotation of the lower joints 130 and the angles sensed by the rotational position sensors 160 on the three joints 130 together determine the positions relative to the base 170 of the centers of rotation of the upper joints 120 for these links 110. The locations of the centers of rotation of the three upper joints 120 define the location of the end platform 100. If the axis of rotation of one of the links 110 relative to the upper yoke 131 of the lower joint 130 does not coincide with the center of rotation of the cross piece 133 of the lower joint 130 to which it is connected, an additional rotational position sensor 160 can be installed on each of the three lower joints 130 to sense the rotation of the corresponding link 110 in the corresponding bearing 134.

The position of the end platform 100 can also be determined using four rotational position sensors (two rotational position sensors 160 like those shown in FIG. 8 mounted on two of the lower joints 130 rather than on three of the joints 130). Given the positions of the centers of rotation of the two lower joints 130 on which the rotational position sensors 160 are mounted, the angles sensed by the four rotational position sensors enable the positions of the centers of rotation of the two corresponding upper joints 120 of the links 110 to be determined. The center of rotation of a third one of the upper joints 120 lies on a circle of known radius containing the centers of rotation of the two upper joints 120 for which the positions are known. The distance of the center of rotation of the third upper joint 120 lies on a sphere of known radius centered at the center of rotation of the lower joint 130 of the corresponding link 110, the radius of the sphere being determined by the length of the corresponding link 110. The position of the center of rotation of the third joint can be determined by calculating the two points of intersection of the circle with the sphere. It can be readily determined from the geometry of the mechanism which of the two possible intersections points is the actual location of the center of rotation of the third upper joint 120. Once the positions of the centers of rotation of the three upper joints 120 are determined, the position of the end platform 100 is known.

Yet another method of determining the position of the end platform 100 is to employ five rotational position sensors installed on a single link 110. Namely, three rotational position sensors 160 can sense rotation of the link 110 about the three axes of rotation of the lower joint 130 of the link 110 while two more rotational position sensors 160 can sense the rotation of the upper end of the link 110 with respect to the end platform 100 about the two axes of rotation of the upper joint 120. Given the location of the center of rotation of the lower joint 130 of the link as determined by the linear position sensor 150 for the corresponding linear actuator 140, the angle sensed by the five rotational position sensors 160 enable the position of the end platform 100 to be determined.

Some of the information obtained by the various sensors may be unnecessary or redundant for the calculation of the forward kinematics. For example, in the arrangement of FIG. 8, the position of the lower ends of the three links 110 not equipped with rotational position sensors 160 is not necessary for the calculation of the position of the end platform 100. Therefore, linear position sensors 150 for the actuators 140 for these links 110 are unnecessary for the purpose of solving the forward kinematics. However, it may still be desirable to equip these actuators 140 with linear position sensors 150 for control purposes, i.e., to enable each of the actuators 140 to translate the corresponding link 110 by a desired amount.

Another way to determine the position of the end platform 100 is to calculate incremental movements of the end platform 100 starting from a known reference position based on incremental movements of the lower ends of the links 110, as determined by the linear position sensors 150 for the linear actuators 140. The incremental movements of the end platform 100 can then be summed to give an approximate position of the end platform 100. Since this method does not employ rotational position sensors 160 on any of the joints of the mechanism, it enables a reduction in the weight of the mechanism.

Algorithms which can be used in the present invention to solve the forward kinematics are well known in the art and are readily derived from basic geometric principles. A detailed discussion of methods of solving for the forward kinematics of a parallel link mechanism with active links can be found in the paper "Optimal Sensor Placement for Forward Kinematics Evaluation of a 6-DOF Parallel Link Manipulator" by Stoughton and Arai (Proceedings of IEEE/RSJ International Workshop on Intelligent Robots and Systems, IROS '91, Volume 2), and the methods disclosed in that paper may also be employed with the present invention, either with active or passive links. A description of the forward kinematics as well as the inverse kinematics of a six-link parallel mechanism according to the present invention is also found in the Appendix. The inverse kinematic problem is the reverse of the forward kinematic problem and involves solving for the positions of the lower joints 130 of the links 110 of a parallel mechanism given the position and orientation of the end platform 100 of the mechanism.

If the current location and orientation of the end platform 100 are known from the forward kinematics, the movement of the lower joints 130 by the linear actuators 140 from their current positions required to move the end platform 100 from its current location and orientation to a new location and/or orientation can be found by determining, based on the inverse kinematics, the displacement of the lower joints 130 from a reference position corresponding to the new location and/or orientation, and subtracting the calculated new displacements from the current displacements for the same joints 130.

A parallel mechanism according to the present invention is very suitable for use as a master device in a master-slave teleoperated system because it can provide the operator with accurate feedback of the forces being applied to the slave device. The slave device can be any desired mechanism, such as another parallel mechanism according to the present invention. An example of master-slave operation in which both the master and the slave are parallel mechanisms similar to the ones shown in FIG. 8 is as follows. The two mechanisms may be of the same or different sizes from each other, with the master being either larger or smaller than the slave. Making the master smaller than the slave is useful when it is desired for the slave to magnify the movements of the master, such as when the slave is being used to move objects large distances. On the other hand, making the master larger than the slave is useful when it is desired for the slave to perform microscopic motions which are too fine for an operator to perform by hand. For example, in microassembly, manual movement of the end platform of the master on the order of millimeters by the operator can be scaled down to movement of the slave on the order of micrometers. However, scaling (either magnifying or decreasing) the motions of the slave relative to those of the master can also be performed when the master and the slave are the same size. Controlling the slave so as to follow the motions of the master is easier if the master and the slave are geometrically similar, although geometric similarity is not required for master-slave operation. The master typically will not be equipped with a tool plate, but it may be equipped with a handle or other member which can be grasped by the operator when manipulating the master. When the operator manipulates the end platform of the master to produce a translation or rotation of the end platform, one or more of the lower joints of the links of the master will undergo translation, and the linear position sensor associated with each joint will sense the new positions of the lower joints. Signals indicative of the new positions will be input to a controller, and the linear actuator associated with each of the corresponding joints of the slave will be controlled by the controller to move the corresponding joint of the slave in the same direction that the corresponding joint of the master was moved but by an amount scaled by the relative sizes of the master and the slave or other scale factor and adjusted in accordance with any dissimilarities in the geometries of the master and the slave so that the end platform of the slave will emulate the movement of the end platform of the master. If the force-torque transducer on the slave does not sense any forces or torques, the forces exerted by the linear actuators of the master will be such as to maintain the end platform of the master stationary in any position in which it has been left by the operator, so as the operator manipulates the end platform, he will feet only the frictional resistance to movement of the master. However, if a force or torque is exerted on the slave, these forces or torques are converted to an equivalent set of forces exerted by the slave actuators on the lower joints of the links using the kinematic equations found in the Appendix, for example. These forces are then scaled as desired, and the controller controls the actuators of the master to apply these scaled forces on the lower joints of the master. In this way, the human operator feels the forces encountered by the slave.

If the slave device is a device having very little friction, such as a parallel mechanism according to the present invention, force feedback can be applied to the master device in the following manner without using the force/torque transducer. The controller drives the actuators on the master so as to decrease any error between the positions of the lower joints on the master and the positions of the corresponding lower joints of the slave. For example, in proportional control of the master and slave, the force exerted on one of the lower joints of the master by the corresponding actuator is the sum of a predetermined value dependent upon the weight of the end platform of the master and a value proportional to the error between the position of the lower joint of the master and the position of the corresponding lower joint of the slave, while the force exerted on one of the lower joints of the slave by the corresponding actuator is the sum of a predetermined value dependent upon the unloaded weight of the end platform of the slave and a value proportional to the error between the position of the lower joint of the slave and the position of the corresponding lower joint of the master. When the slave is able to move freely without obstacles and its end platform is unloaded, the positions of the master and slave correspond very closely, and the operator feels only the frictional forces in moving the devices, which can be made very small when the master and slave arc mechanisms according to the present invention. However, when the slave picks up an object, the weight of the object creates a difference between the positions of the lower joints of the master and the slave. Due to the difference in positions, the controller increases the forces exerted by the actuators of the slave, enabling the actuators to support the object, but at the same time, the controller increases the forces exerted by the actuators of the master by an amount proportional to the difference in positions and therefore proportional to the weight of the object, thereby enabling the operator of the master to sense the weight of the object. Depending upon the method of control which is employed, the actuators of the master can continue to exert a force proportional to the weight of the object on the hand of the operator, or the forces exerted by the actuators of the master can be gradually returned to their initial values so that the operator senses the weight of the object only when it is first picked up. Similarly, if the slave encounters constraints within its environment (such as when the slave contacts an immovable object), the constraint forces create small differences in the positions of the joints of the slave and the corresponding joints of the master, so the controller increases the forces exerted by the actuators of the master, whereby the operator feels the constraint forces encountered by the slave.

What is claimed is:

1. A parallel mechanism for manipulating an object in space comprising:

a platform for supporting an object to be manipulated;

a plurality of links each having a first end movably connected to the platform and a second end spaced from the platform with the platform being kinematically restrained by the links;

a plurality of first rotatable joints each rotatably connecting the first end of one of the links to the platform and a plurality of second rotatable joints each connected to the second end of one of the links, each of the first joints having a center of rotation located on a first circle with a first axis and each of the second joints having a center of rotation, the mechanism having a reference position in which the center of rotation of each of the second joints is located on a second circle coaxial with and spaced from the first circle, a line connecting the centers of rotation of the first and second joints of each link crossing a line connecting the centers of rotation of the first and second joints of another of the links when the mechanism is in the reference position and viewed along the first axis;

a plurality of linear motors each associated with one of the links and having a movable portion capable of translating the first end of one of the links to move the platform;

a rotatable support member rotatably supported by the platform; and a drive member for rotating the rotatable support member spaced from the platform and drivingly connected to the rotatable support member.

2. A parallel mechanism as claimed in claim 1 wherein each of the linear motors is rotatably connected to the second end of one of the links.

3. A parallel mechanism as claimed in claim 2 wherein the movable portions of the linear motors are movable parallel to a common axis.

4. A parallel mechanism as claimed in claim 2 wherein each of the linear motors is a moving coil linear motor.

5. A parallel mechanism as claimed in claim 3 including a plurality of linear guides each supporting the movable portion of one of the linear motors for movement parallel to the common axis.

6. A parallel mechanism as claimed in claim 5 wherein each linear guide movably supports a coil of one of the linear motors.

7. A parallel mechanism as claimed in claim 1 wherein the first end of each link is rotatably connected to the platform.

8. A parallel mechanism as claimed in claim 1 including a base supporting the second ends of the links, the drive member being mounted on the base.

9. A parallel mechanism as claimed in claim 1 wherein the drive member is connected to the rotatable support member in a manner enabling the drive member to rotate the rotatable support member at varying angles and positions of the platform relative to the drive member.

10. A parallel mechanism as claimed in claim 1 wherein the rotatable support member has an axis of rotation which is fixed with respect to the platform.

11. A parallel mechanism as claimed in claim 10 wherein the rotatable support member comprises a support plate for supporting an object rotatably mounted on the platform.

12. A parallel mechanism as claimed in claim 1 wherein the drive member comprises a rotary actuator, the mechanism including a drive shaft for transmitting torque from the rotary actuator to the rotatable support member and capable of translating with respect to the rotary actuator in an axial direction of the drive shaft as the drive shaft is rotating.

13. A parallel mechanism as claimed in claim 12 including a ball spline connected between the drive shaft and the rotary actuator.

14. A parallel mechanism as claimed in claim 9 including a universal joint connected between the drive member and the rotatable support member to enable an angle between the drive member and the rotatable support member to vary.

15. A parallel mechanism as claimed in claim 1 further including a plurality of sensors each associated with one of the linear motors for generating a signal indicative of movement of the movable portion of the linear motor.

16. A parallel mechanism as claimed in claim 15 further including a slave mechanism controlled by the parallel mechanism.

17. A parallel mechanism for manipulating an object in space comprising:
   a platform for supporting an object to be manipulated;
   a plurality of links each having a first end rotatably connected to the platform and a second end spaced from the platform, the platform being kinematically restrained by the links, at least one of the links being a nonlinear link having a portion not coinciding with a straight line between the first and second ends of the link;
   a plurality of linear motors each associated with one of the links for translating the first ends of the links to move the platform;
   a rotatable support member rotatably supported by the platform; and
   a drive member for rotating the rotatable support member spaced from the platform and drivingly connected to the rotatable support member.

18. A parallel mechanism as claimed in claim 17 wherein each of the links is a nonlinear link.

19. A parallel mechanism as claimed in claim 17 including six links, at least three of which are nonlinear links.

20. A parallel mechanism as claimed in claim 17 wherein the nonlinear link has a curved region between its first and second ends.

21. A parallel mechanism as claimed in claim 17 including a plurality of first rotatable joints each rotatably connecting the first end of one of the links to the platform and a plurality of second rotatable joints each connected to the second end of one of the links, each of the first and second joints having a center of rotation where two axes of rotation of the joint intersect, the mechanism having a reference position in which the centers of rotation of the first joints lie in a first plane, the centers of rotation of the second joints lie in a second plane parallel to the first plane, and for each link, a line connecting the centers of rotation of the first and second joints of the link intersects a line connecting the centers of rotation of the first and second joints of another of the links, none of the links intersecting each other in the reference position.

22. A parallel mechanism as claimed in claim 21 wherein each link does not contact any of the other links when the mechanism is in the reference position.

23. A parallel mechanism for manipulating an object in space comprising:
   first through sixth links each having a first end and a second end;
   a platform kinematically restrained by the links for supporting an object to be manipulated;
   a plurality of first rotatable joints each rotatably connecting the first end of one of the links to the platform and a plurality of second rotatable joints each connected to the second end of one of the links, each of the first and second joints having a center of rotation where two axes of rotation of the joint intersect; and
   an actuator associated with each link for translating the first ends of the links to move the platform,
   the centers of rotation of the first joints being spaced at substantially equal angular intervals about a first axis, and the centers of rotation of the second joints being spaced at substantially equal angular intervals about a second axis wherein the mechanism has a reference position in which the centers of rotation of the first joints lie in a first plane and the centers of rotation of the second joints lie in a second plane parallel to the first plane and the centers of rotation of the first joints are located on two concentric and coplanar circles.

24. A parallel mechanism as claimed in claim 23 wherein the centers of rotation of the first joints lie on a first circle and the centers of rotation of the second joints lie on a second circle coaxial with and axially spaced from the first circle when the mechanism is in the reference position.

25. A parallel mechanism as claimed in claim 23 wherein the centers of rotation of the second joints are located on two concentric and coplanar circles when the mechanism is in the reference position.

26. A parallel mechanism as claimed in claim 23 wherein when the mechanism is in the reference position, the first and second axes are coincident, the centers of rotation of the first joints of the first through sixth links are located at angles of approximately 0, 60, 120, 180, 240, and 300 degrees, respectively, with respect to the axes, and the centers of rotation of the second joints of the first through sixth links are located at angles of approximately 60, 0, 180, 120, 300, and 240 degrees, respectively, with respect to the axes when the mechanism is viewed along the axes, taking a location of an arbitrary one of the first joints as 0 degrees.

27. A parallel mechanism for manipulating an object in space comprising:

first through sixth links each having a first end and a second end;

a platform kinematically restrained by the links for supporting an object to be manipulated;

a plurality of first rotatable joints each rotatably connecting the first end of one of the links to the platform and a plurality of second rotatable joints each connected to the second end of one of the links, each of the first and second joints having a center of rotation where two axes of rotation of the joint intersect; and an actuator associated with each link for translating the first ends of the links to move the platform, the centers of rotation of the first joints being spaced at substantially equal angular intervals about a first axis, and the centers of rotation of the second joints being spaced at substantially equal angular intervals about a second axis, wherein the mechanism has a reference position in which the centers of rotation of the first joints lie in a first plane and the centers of rotation of the second joints lie in a second plane parallel to the first plane and the centers of rotation of the second joints are located on two concentric and coplanar circles when the mechanism is in the reference position.

28. A parallel mechanism as claimed in claim 27 wherein the centers of rotation of the first joints lie on a first circle and the centers of rotation of the second joints lie on a second circle coaxial with and axially spaced from the first circle when the mechanism is in the reference position.

29. A parallel mechanism as claimed in claim 27 wherein when the mechanism is in the reference position, the first and second axes are coincident, the centers of rotation of the first joints of the first through sixth links are located at angles of approximately 0, 60, 120, 180, 240, and 300 degrees, respectively, with respect to the axes, and the centers of rotation of the second joints of the first through sixth links are located at angles of approximately 60, 0, 180, 120, 300, and 240 degrees, respectively, with respect to the axes when the mechanism is viewed along the axes, taking a location of an arbitrary one of the first joints as 0 degrees.

\* \* \* \* \*